US008153772B2

(12) United States Patent
Brown et al.

(10) Patent No.: US 8,153,772 B2
(45) Date of Patent: Apr. 10, 2012

(54) OLIGONUCLEOTIDE PROBES AND PRIMERS COMPRISING UNIVERSAL BASES FOR DIAGNOSTIC PURPOSES

(75) Inventors: Bob D. Brown, Encinitas, CA (US); Timothy A. Riley, San Diego, CA (US)

(73) Assignee: Gen-Probe Incorporated, San Diego, CA (US)

(*) Notice: Subject to any disclaimer, the term of this patent is extended or adjusted under 35 U.S.C. 154(b) by 418 days.

(21) Appl. No.: 10/375,504

(22) Filed: Feb. 25, 2003

(65) Prior Publication Data

US 2003/0170711 A1 Sep. 11, 2003

Related U.S. Application Data

(63) Continuation of application No. 10/142,729, filed on May 8, 2002, now abandoned, and a continuation-in-part of application No. 09/136,080, filed on Aug. 18, 1998, now Pat. No. 6,518,017.

(60) Provisional application No. 60/306,229, filed on Jul. 18, 2001, provisional application No. 60/060,673, filed on Oct. 2, 1997.

(51) Int. Cl.
C07H 21/04 (2006.01)
C07H 21/02 (2006.01)

(52) U.S. Cl. ..................................... 536/23.1

(58) Field of Classification Search .................. None
See application file for complete search history.

(56) References Cited

U.S. PATENT DOCUMENTS

| | | | |
|---|---|---|---|
| 4,458,066 A | 7/1984 | Caruthers et al. | 536/25.34 |
| 4,683,194 A | 7/1987 | Saiki et al. | 435/6 |
| 5,104,792 A | 4/1992 | Silver et al. | 435/6 |
| 5,112,974 A | 5/1992 | Barton | 546/4 |
| 5,223,618 A | 6/1993 | Cook et al. | 544/276 |
| 5,378,825 A | 1/1995 | Cook et al. | 536/25.34 |
| 5,424,413 A | 6/1995 | Hogan et al. | 536/25.31 |
| 5,438,131 A | 8/1995 | Bergstrom et al. | 536/28.6 |
| 5,451,503 A | 9/1995 | Hogan et al. | 435/6 |
| 5,489,677 A | 2/1996 | Sanghvi et al. | 536/22.1 |
| 5,500,357 A * | 3/1996 | Taira et al. | 435/91.31 |
| 5,539,082 A | 7/1996 | Nielsen et al. | 530/300 |
| 5,541,307 A | 7/1996 | Cook et al. | 536/23.1 |
| 5,550,357 A | 8/1996 | Huang | 165/104.34 |
| 5,571,902 A | 11/1996 | Ravikumar et al. | 530/22.1 |
| 5,571,903 A | 11/1996 | Gryaznov | 536/23.1 |
| 5,583,032 A | 12/1996 | Torrence et al. | 435/91.1 |
| 5,612,199 A | 3/1997 | Western et al. | 435/91.1 |
| 5,612,215 A | 3/1997 | Draper et al. | 435/366 |
| 5,623,065 A | 4/1997 | Cook et al. | 536/23.1 |
| 5,627,032 A | 5/1997 | Ulanovsky | 435/6 |
| 5,646,042 A | 7/1997 | Stinchcomb et al. | 435/366 |
| 5,650,271 A | 7/1997 | Richards | 435/6 |
| 5,677,289 A | 10/1997 | Torrence et al. | 514/44 |
| 5,681,702 A | 10/1997 | Collins et al. | 435/6 |
| 5,681,947 A | 10/1997 | Bergstrom et al. | 536/28.6 |
| 5,683,879 A | 11/1997 | Laney et al. | 435/6 |
| 5,686,242 A | 11/1997 | Bruice et al. | 435/6 |
| 5,700,922 A | 12/1997 | Cook | 536/23.1 |
| 5,719,271 A | 2/1998 | Cook et al. | 536/23.1 |
| 5,728,818 A | 3/1998 | Wincott et al. | 536/25.3 |
| 5,780,233 A | 7/1998 | Guo et al. | 435/6 |
| 5,780,610 A | 7/1998 | Collins et al. | 536/24.5 |
| 5,831,066 A | 11/1998 | Reed | 536/24.5 |
| 5,840,845 A | 11/1998 | Smith et al. | 530/350 |
| 5,843,650 A | 12/1998 | Segev | 435/6 |
| 5,872,242 A | 2/1999 | Monia et al. | 536/24.5 |
| 5,877,162 A | 3/1999 | Werner et al. | 514/44 |
| 5,898,031 A | 4/1999 | Crooke | 435/91.3 |
| 5,929,040 A | 7/1999 | Werther et al. | 514/44 |
| 5,942,657 A | 8/1999 | Bird et al. | 800/284 |
| 5,952,202 A | 9/1999 | Aoyagi et al. | 435/91.2 |
| 5,968,748 A | 10/1999 | Bennett et al. | 435/6 |
| 5,981,179 A | 11/1999 | Lorinez et al. | 435/6 |
| 6,025,130 A | 2/2000 | Thomas et al. | 435/6 |
| 6,027,893 A | 2/2000 | Ørum et al. | 435/6 |
| 6,037,130 A | 3/2000 | Tyagi et al. | 435/6 |
| 6,077,833 A | 6/2000 | Bennett et al. | 514/44 |
| 6,084,102 A | 7/2000 | Kutyavin et al. | 548/100 |
| 6,107,094 A | 8/2000 | Crooke | 435/455 |
| 6,133,031 A | 10/2000 | Monia et al. | 435/375 |
| 6,150,141 A | 11/2000 | Jarrell | 435/91.31 |
| 6,159,694 A | 12/2000 | Karras | 435/6 |
| 6,172,216 B1 | 1/2001 | Bennett et al. | 536/24.5 |
| 6,194,158 B1 | 2/2001 | Kroes et al. | 435/6 |
| 6,197,556 B1 | 3/2001 | Ulanovsky et al. | 435/91.2 |
| 6,201,107 B1 | 3/2001 | Lap-Chee et al. | 530/387.1 |

(Continued)

FOREIGN PATENT DOCUMENTS

WO    WO 89/02921    4/1989

(Continued)

OTHER PUBLICATIONS

Five Kingdoms, An Illustrated Guide to the Phyla of Life on Earth, Second Edition, Margulis et al, 1988, W.H. Freeman and Company, New York, p. 3.* |National Center for Biotechnology Information, Entrez Genome Project (www.National Center for Biotechnology Information.nlm.gov/genomes/Iproks.cgi Jan. 7, 2007).*
Genetics and the Logic of Evolution, Weiss et al, 2004, John Wiley & Sons, Inc., pp. 105-107.*
The Extended Phenotype, Dawkins, 1982, Oxford University Press, Oxford, pp. 81-96.*
Chemical Abstracts and Indexes, American Chemical Society, Columbus, US, XP000376987, ISSN: 0009-2258, (1990).
Amosova et al. "Effect of the 1-(2'-deoxy-Beta-D-ribofuranosyl)-3-Nitropyrrole Residue on the Stability of DNA Duplexes and Triplexes," *Nucleic Acids Research*, 25(10):1930-1934 (1997).
Benseler et al., "Hammerhead-like Molecules Containing Non-Nucleotide Linkers are Active RNA Catalysts," *J. Am. Chem. Soc.*, 115:8483-8484, (1993).
Bergstrom et al., "Synthesis, Structure, and Deoxyribonucleic Acid Sequencing with a Universal Nucoeside: 1-(2'-Deoxy-β-D-Ribofuranosyl)-3-nitropyrrole," *J. Am. Chem. Soc.*, 117:1201-1209 (1995).

(Continued)

*Primary Examiner* — James Martinell

(74) *Attorney, Agent, or Firm* — Foley & Lardner LLP; Stephen E. Reiter

(57) ABSTRACT

Aspects of the invention relate to novel oligonucleotides comprising universal and generic bases for use as primers and probes, as well as, methods of using said oligonucleotides for the diagnosis of disease.

23 Claims, 1 Drawing Sheet

U.S. PATENT DOCUMENTS

| | | | |
|---|---|---|---|
| 6,228,642 B1 | 5/2001 | Baker et al. | 435/375 |
| 6,232,079 B1 | 5/2001 | Wittwer et al. | 435/6 |
| 6,232,462 B1 | 5/2001 | Collins et al. | 536/25.3 |
| 6,287,772 B1 | 9/2001 | Stefano et al. | 435/6 |
| 6,346,614 B1 | 2/2002 | Metelev et al. | 536/25.3 |
| 6,346,938 B1 | 2/2002 | Chan et al. | 345/419 |
| 6,361,940 B1 | 3/2002 | Van Ness et al. | 435/6 |
| 6,372,427 B1 | 4/2002 | Kanimalla et al. | 435/6 |
| 6,379,932 B1 | 4/2002 | Arnold et al. | 435/91.51 |
| 6,380,368 B1 | 4/2002 | Froehler et al. | 536/22.1 |
| 6,391,593 B1 | 5/2002 | Weston et al. | 435/91.2 |
| 6,451,588 B1 | 9/2002 | Egholm et al. | 435/287.2 |
| 6,465,193 B2 | 10/2002 | Akeson et al. | 435/7.1 |
| 6,518,017 B1 | 2/2003 | Riley et al. | 435/6 |
| 6,620,584 B1 * | 9/2003 | Chee et al. | 435/6 |
| 6,623,962 B1 | 9/2003 | Akhtar et al. | 435/375 |
| 6,905,820 B2 | 6/2005 | Uhlmann et al. | 435/6 |
| 7,223,536 B2 * | 5/2007 | Wright et al. | 435/6 |

FOREIGN PATENT DOCUMENTS

| | | |
|---|---|---|
| WO | WO 91/15601 | 10/1991 |
| WO | WO 93/05175 | 3/1993 |
| WO | WO 93/05176 | 3/1993 |
| WO | WO 93/06240 | 4/1993 |
| WO | WO 93/10103 | 5/1993 |
| WO | WO 93/23551 | 11/1993 |
| WO | WO 94/06810 | 3/1994 |
| WO | WO 94/09129 | 4/1994 |
| WO | WO 95/01985 | 1/1995 |
| WO | WO 96/32474 | 10/1996 |
| WO | WO 97/18312 | 5/1997 |
| WO | WO 97/26270 | 7/1997 |
| WO | WO 97/28177 | 8/1997 |
| WO | WO 97/33991 | 9/1997 |
| WO | WO 97/38097 | 10/1997 |
| WO | WO 97/46711 | 12/1997 |
| WO | WO 98/58057 | 12/1998 |
| WO | WO 99/13886 | 3/1999 |
| WO | WO 99/18238 | 4/1999 |
| WO | WO 00/61810 | 10/2000 |

OTHER PUBLICATIONS

Blommers et al. "Effects of the Introduction of L-Nucleotides into DNA. Solution Structure of the Heterochiral Duplex d(G-C-G-(L)T-G-C-G) d(C-G-C-A-C-G-C) Studied by NMR Spectroscopy," *Biochemistry*, 33:1886-1896 (1994).

Bolufer et al. "Rapid Quantative Detection of BCR-ABL transcripts in chronic myeloid leukemia patients by real-time reverse transcriptase polymerase-chain reaction using fluorescently labeled probes," *Haematologica*, 85(12):1248-1254 (2000).

Brown et al. "Synthesis and duplex stability of oligonucleotides containing adenine-guanine analogues," *Carbohydrate Res*, 216:129-139 (1991).

Chen et al., "Synthesis of Oligodeoxyribonucleotide N3'-P5' Phosphoramidates," *Nucleic Acids Research*, 23(14):2661-2668 (1995).

Chiang et al., "Antisense oligonucleotides inhibit intercellular adhesion molecule 1 expression by two distinct mechanisms," *J. Biol. Chem.*, 266(27):18162-18171 (1991).

Devaney et al. "Genotyping of two mutations in the HFE gene using single-base extension and high-performance liquid chromatography," *Anal. Chem.*, 73(3): 620-624 (2001).

Donohue et al., "Rapid single-tube screening of the C282Y hemochromatosis mutation by real-time multiplex allele-specific PCR without fluorescent probes," *Clinical Chemistry*, 46(10):1540-1547 (2000).

Dueholm et al., "Synthesis of Peptide Nucleic Acid Monomers Containing the Four Natural Nucleobases: Thymine, Cytosine, Adenine, and Guanine and their Oligomerization," *J Org Chem.*, 59:5767-5773 (1994).

Eritja et al., "Synthesis and properties of defined DNA oligomers containing base mispairs involving 2-aminopurine," *Nucleic Acids Research*, 14(14):5869-5884 (1986).

Frutos et al. "Method for Detection of Singel-Base Mismatches Using Bimolecular Beacons," *J. Am. Chem. Soc.*, 124(11):2396-2397 (Received for publication Oct. 16, 2001) Published Feb. 26, 2002.

Guttridge et al. "Population Screening for Hemochromatosis by PCR Using Sequence-Specific Primers," *Genetic Testing*, 4(2):111-114 (2000).

Hartmann et al., "Specific suppression of human tumor necrosis factor-α synthesis by antisense oligodeoxynucleotides," *Antisense and Nucleic Acid Drug Development*, 6:291-299 (1996).

Heim et al., "Highly sensitive detection of gene expression of an intronless gene: amplification of mRNA, but not genomic DNA by nucleic acid sequence based amplification (NASBA)," *Nucleic Acids Research*, 26(9):2250-2251 (1998).

Hendry et al. "Using Linkers to Investigate the Spatial Separation of the Conserved Nucleotides A9 and G12 in the Hammerhead Ribozyme," *Biochimica et Biophysica Acta*, 1219(2):405-412 (1994).

Izant and Weintraub, "Inhibition of thymidine kinase gene expression by anti-sense RNA: a molecular approach to genetic analysis," *Cell*, 36:1007-1015 (1984).

Krupp G., "Antisense Oligoribonucleotides and RNAse P. A Great Potential," *Biochimie* 75(112):135-139 (1993).

Kunitsyn et al. "Stabilizing Effect of 5-Nitroindole (Universal Base) on DNA Duplexes Immobilized on Gel Matrix," *J. of Biomolec. Structure and Dynamics*, 15(3):597-603 (1997).

Lieber et al. "Selection of Efficient Cleavage Sites in Target RNAs by Using a Ribozyme Expression Library," *Molecule and Cellular Biology*, 15(1):540-551 (1995).

Lin and Brown, "Synthesis and duplex stability of oligonucleotides containing cystosine-thymine analogues," *Nucleic Acids Research*, 17(24)10373-10383 (1989).

Lin and Brown, "Synthesis of oligodeoxyribonucleotides containing degenerate bases and their use as primers in the polymerase chain reaction," *Nucleic Acids Research*, 20(19):5149-5152 (1992).

Lizardi et al., "Mutation detection and single-molecule counting using isothermal rolling-circle amplification," *Nature Genet.*, 19:225-232 (1998).

Loakes, "3-Nitropyrrole and 5-Nitroindole as Universal Bases in Primers for DNA Sequencing and PCR," *Nucleic Acids Research*, 23(13):2361-2366 (1995).

Ma et al., "Nuclease-resistant external guide sequence-induced cleavage of target RNA by human ribonuclease P," *Antisense and Nuclic Acid Drug Development.*, 8:415-426 (1998).

McCurdy et al., "An Improved Method for the Synthesis of N3'-P5' Phosphoramidate Oligonucleotides," *Tetrahedron Lett*, 38(2):207-210 (1997).

Medintz et al. "High speed single nucleotide polymorphism typing of a hereditary haemochromatosis mutation with capillary array electrophoresis microplates," *Electrophoresis*, 21:2352-2358 (2000).

Milligan et al. "Current Concepts in Antisense Drug Design" *J. Medicinal Chemistry*, 36(14):1923-1937 (1993).

Morvan et al., "Oligonucleotide Mimics for Antisense Therapeutics: Solution Phase and Automated Solid-Support Synthesis of MMI Linked Oligomers," *J Am Chem Soc*, 118:255-256 (1996).

Mueller et al, "Self-sustained sequence replication (3SR): an alternative to PCR," *Histochem. Cell Biol.*, 108:431-437 (1997).

Nelson et al., "N3'-P5' Oligodeoxyribonucleotide Phosphoramidites: A New Method of Synthesis Based on a Phosphoramidite Amine-Exchange Reaction," *J. Org. Chem.*, 62:7278-7287 (1997).

Nichols et al., "A Universal Nulceoside for Use at Ambiguous Sites in DNA Primers" *Nature*, 369:492-493 (1994).

Perbost et al., "Synthesis of 5'-O-Amino-2'deoxypyrimidine and Purine Nucleosides: Building Blocks for Antisense Oligonucleotides," *J. Org. Chem.*, 60:5150-5156 (1995).

Pierce et al. "Construction of a Directed Hammerhead Ribozume Library: Towards the Identification of Optimal Target Sites for Antisense-Mediated Gene Inhibition," *Nucleic Acids Research*, 26(22):5093-5101 (1998).

Pitsch et al., "Why Pentose and Not Hexose-Nucleic Acids?" *Helv Chemica Acta*, 76:2161-2183 (1993).

Press, R., "Detection of Prevalent Generic Alterations Predisposing to Hemochromatosis and Other Common Human Diseases," Clinical Chem. 46:1526-1527 (2000).

Restagno et al. "A Pilot C282Y Hemocheromatosis Screening in Italian Newborns by TaqMan (TM) Technology," *Genetic Testing*, 4(2):177-181 (2000).

Reynolds et al. "Antisense Oligonucleutides Containinf an Internal, Non-nucleotide-based Linker Promote Site-Specific Cleavage of RNA," *Nucleic Acids Research*, 24(4):760-765 (1996).

Romano et al., "NASBA technology: isothermal RNA amplification in qualitative and quantitative diagnostics," *Immunol. Invest.*, 26:15-28 (1997).

Spargo et al, "Detection of *M. tuberculosis* DNA using thermophilic strand displacement amplification," *Mol, Cell Probes*, 10:247-256 (1996).

Swayze et al., "The Synthesis of N,N'-O'Trisubstituted Hydroxylamines via a Mild Reductive Alkylation Procedure: An Improved Synthesis of the MMI Backbone," *Synlett*, pp. 859-861 (1997).

Van Aerschot et al. "An Acyclic 5-Nitroindazole Nucleoside Analogue as Ambiguous Nucleoside," *Nucleic Acids Research*, 23(21):4363-4370 (1995).

Walker, "Empirical aspects of strand displacement amplification," *PCR Methods Applications*, 3:1-6 (1993).

Zhong and Kallenbach, "Conformation and Thermodynamics of DNA 'Necks' Models for Three-arm Branch Formation in a Duplex," *J. Mol. Biol.*, 230:766-778 (1993).

Zhong et al., "Effects of Unpaired Bases on the Conformation and Stability of Three-Arm DNA Junctions," *Biochemistry*, 33:3660-3667 (1994).

PCT International Search Report, PCT/US00/09293 in 4 pages, Aug. 8, 2000.

PCT International Preliminary Examination Report, PCT/US00/09293 in 6 pages, Jun. 29, 2001.

Supplementary Partial European Search Report, EP 00 92 1855 in 9 pages, Sep. 19, 2003.

PCT International Search Report, PCT/US00/09230 in 5 pages, Jul. 24, 2000.

PCT International Preliminary Examination Report, PCT/US98/20361 in 7 pages, Jan. 20, 2000.

PCT International Search Report, PCT/US98/20361 in 5 pages, Feb. 2, 1999.

Supplementary Partial European Search Report, EP 98 94 8573 in 5 pages, Oct. 15, 2004.

International Search Report, PCT/US93/10103 in 2 pages, Jul. 4, 1998.

Agrawal et al Antisense therapeutics: Is it as simple as complementary base recognition? *Molecular Medicine Today*, 2000 Vp; 6:72-81.

Altmann et al, "Novel Chemistry," *Applied Oligonucleotide Technology*, Chapter 4, pp. 73-107 (1998).

Branch, AD A good antisense moleucle is hard to find *TIBS*, 1998 vol. 23:45-50.

Deb et al RNA-Dependent Protein Kinase PKR is required for activation of NF-kappa B by IFN-gamma in a STAT1-independent pathway *Journal of Immunology*, 2001 vol. 166:6170-6180.

Hill et al, "Polymerase recognition of synthetic oligodeoxyribnucleotides incorporation degenerate pyrimidine and purine bases," *Proc Natl Acad Sci USA*, 95:4258-4263 (1998).

Jen et al Suppression of gene expression by targeted disruption of messenger RNA: available options and current strategies *Stem Cells*, 2000 vol. 18:307-319.

Kuwabara et al "Activities of tRNA-embedded dimeric minizymes," *Nucleic Acids Symposium Series*, No. 37: 307-308 (1997).

Parker et al, "Ribozymes: Principles and Designs for Their Use as Antisense and therapeutic Agents," Gene Regulation: Biology of Antisense RNA and DNA, New York, *Raven Press*, pp. 55-70 (1992).

Sanghvi, "Heterocyclic Base Modifications in Nucleic Acids and Their Applications in Antisense Oligonucleotides," *Antisense Research and Applications, CRC Press*, GB, Chapter 15, pp. 273-288 (1993).

Thomson et al "Universal base analogs in antisense oligodeoxynucleotides (as ODNs) : A therapeutic stratedy against HIV variability," *American Society for Microbiology*, p. 143 (1995).

Tidd, Ed DM "Ribonuclease H-Mediated Antisense Effects of Oligonucleotides and Controls for Antisense Experiments," *Applied Antisense Oligonucleotide Technology*, pp. 161-171 (1998).

Cole et al., "Activation of RNase L by 2',5'-Oligoadenylates," J Biol Chem. Aug. 1;272(31):19187-92 (1997).

Kurreck et al. Design of antisense oligonucleotides stabilized by locked nucleic acids. Nucleic Acids Research, vol. 30:1911-1918 (2002).

Li, Y. et al., "Targeted Cleavage of mRNA in vitro by Rnase P from *Escherichia coli*." Proc. Natl. Acad. Sci. USA. Apr. 15; 89: 3185-3189 (1992).

Loakes et al., "5-nitroindole as an universal base," Nucleic Acids Research, 1994: vol. 22 No. 20: 4039-4043. Oxford University Press (1994).

Skerra, A. Phosphorothioate primers improve the amplification of DNA sequences by DNA polymersases with proofreading activity. Nucleic Acids Research, 1992 vol. 20:3551-3554.

Walder et al., "Role of Rnase H in hybrid-arrested translation by antisense oligonucleotides," Proc. Natl. Acad. Sci. vol. 85: 5011-5015 (1988).

"Antisense Technology; Patent Claims Allowed for Therapy Targeted Against Gene," *Blood Weekly*, Atlanta; Nov. 18, 1996, pp. 6-7 (reprint from ProQuest: 2 pages total).

Brookes, Anthony J., "The essence of SNPs," *Gene*, 234:177-186 (1999).

* cited by examiner

I. Demonstration using Melting Temperature Determinations-

Natural Probe on matching and single-base-mismatch targets:

```
T_M = 71°C Perfect Match
5'   gagctGctaactgagcacAgg            -Natural Probe OGC2      (SEQ ID NO:2)
     |||||||||||||||||||||
3'   tactcgaCgattgactcgtgTcctactggaccctggg  -Matching target   (SEQ ID NO:7)

T_M = 65°C with a single mismatch (-6°C relative to perfect match)
5'   gagctGctaactgagcacAgg            -Natural Probe OGC2      (SEQ ID NO:2)
     |||||x|||||||||||||||
3'   tactcgaGgattgactcgtgTcctactggaccctggg  -Mis-match target  (SEQ ID NO:8)
```

GeneLead™ Probe on matching and single-base-mismatch targets:

```
T_M = 55°C Perfect Match with Universal Bases
5'   gagctGctaaBBBBBcacAgg            -GeneLead™ Probe OGX2    (SEQ ID NO:4)
     |||||||||      ||||||
3'   tactcgaCgattgactcgtgTcctactggaccctggg  -Matching target   (SEQ ID NO:7)

T_M = 38°C with a single mismatch (-17°C relative to perfect match)
5'   gagctGctaaBBBBBcacAgg            -GeneLead™ Probe OGX2    (SEQ ID NO:4)
     |||||x|||      ||||||
3'   tactcgaGgattgactcgtgTcctactggaccctggg  -Mis-match target  (SEQ ID NO:8)
```

OLIGONUCLEOTIDE PROBES AND PRIMERS COMPRISING UNIVERSAL BASES FOR DIAGNOSTIC PURPOSES

RELATED APPLICATIONS

This application is a continuation of U.S. patent application Ser. No. 10/142,729 filed May 8, 2002 now abandoned, which claims priority to U.S. Provisional Application 60/306229, filed Jul. 18, 2001. This application is also a continuation-in-part of application Ser. No. 09/136,080 filed on Aug. 18, 1998 now U.S. Pat. No. 6,518,017, which claims priority to U.S. Provisional Application 60/060,673 filed on Oct. 2, 1997. This application claims priority to all of the aforementioned applications, the disclosures of which are hereby expressly incorporated by reference in their entireties.

FIELD OF THE INVENTION

Aspects of the invention relate to novel oligonucleotides comprising universal and generic bases for use as primers and probes, as well as, methods of using said oligonucleotides for the diagnosis of disease.

BACKGROUND OF THE INVENTION

The explosion of recent knowledge in basic genetics has spawned numerous clinical follow-up studies that have confirmed an unequivocal association between the presence of specific prevalent genetic alterations and susceptibility to some very common human diseases. In addition, the Human Genome Project's sequencing efforts will contribute yet more candidate disease genes that will require both research-based genetic association studies (to confirm suspected disease links) and, if positive, the translation of these disease-genotype associations to routine diagnostic clinical practice. Given this expanding repertoire of confirmed and reputed disease genes (many for common diseases), the demand for rapid, sensitive, specific, inexpensive assays for their clinical- and/or research-based detection is growing quickly.

As a consequence, clinical genetic testing laboratories, once accustomed to manual, low-volume, high-labor tests on patients with rare, untreatable classic "genetic" diseases, will soon need to develop better high-throughput and semi-automated methods. In the fast-approaching molecular medicine era, these new genotyping methods will be utilized not only for diagnosing symptomatic patients but perhaps, more importantly, for presymptomatically identifying individuals at risk for common, treatable diseases for whom effective preventative interventions may be available.

Oligonucleotide hybridization is a method commonly used in the field of molecular biology for the treatment and diagnosis of disease, as well as the identification, quantitation, and isolation of nucleic acids. Accordingly, it is important to identify methods to increase the specificity and affinity of oligonucleotides for their targets. In this way, diagnostics which provide efficient and precise answers can be made. Various methods for increasing the specificity of oligonucleotides are known in the art, including increasing the length, choosing oligonucleotides that are not likely to cross-hybridize or bind non-specifically and designing oligonucleotides that have a high annealing temperature. (See e.g., Bergstrom et al., *J. Am. Chem. Soc.* 117:1201-1209, 1995; Nicols et al., *Nature* 369:4920493, 1994; Loakes, *Nucl. Acids Res.* 22:4039-4043, 1994; Brown, *Nucl. Acids Res.* 20:5149-5152, 1992).

Recently, investigators have determined that modified oligonucleotides containing universal bases provide some benefit over conventional oligonucleotide chemistries. (See Guo et al., U.S. Pat. No. 5,780,233, filed Jun. 6, 1996). Although Guo et al., observed some improvement in being able to discriminate a variant nucleotide in a target nucleic acid by incorporating solitary universal bases (artificial mismatches) sprinkled throughout a probe oligonucleotide, particular spacing and composition requirements were necessary. For example, Guo et al. found that the universal base should be carefully spaced from the variant nucleotide (i.e., 3 or 4 nucleotides away) and that the oligonucleotide probes should not contain a total composition of universal bases of greater than 15%.

Van Ness et al. (U.S. Pat. No. 6,361,940, filed Apr. 1, 1998) also found that the incorporation of universal bases (specificity spacers) could increase the specificity of a probe oligonucleotide for a target nucleic acid. As above, however, Van Ness et al. determined that the universal bases should be spaced a considerable distance from each other (4-14 nucleotides). Thus, despite the advances made by the investigators above and others in the field, there still remains a need for better oligonucleotide chemistries, which allow for the development of more efficient diagnostics and therapeutics.

SUMMARY OF THE INVENTION

Aspects of the invention concern oligonucleotides having universal or generic bases, which can be used for diagnostic and therapeutic purposes. Unexpectedly, it was discovered that oligonucleotides having a universal or generic base composition of at least 20%-50% of the total number of bases facilitate the identification of mutations and polymorphisms, in particular single nucleotide polymorphisms (SNps). Further, it was also discovered that oligonucleotides having at least 2, 3, 4, 5, 6, 7, 8, 9, 10, 11 or more juxtaposed universal or generic bases facilitate the identification of mutations and polymorphisms, in particular SNPs. The oligonucleotides described herein have many other utilities besides the detection of SNPs including, but not limited to, application in other diagnostic processes, array technology, sequencing, hybridization and other techniques, which use conventional oligonucleotides.

It is further contemplated that placing an unnatural base that has a modified affinity, preferably a higher affinity, but a lower affinity may also be used, increases the ability to differentiate a single nucleotide polymorphism or a polymorphic site from a normal site.

BRIEF DESCRIPTION OF THE DRAWINGS

FIG. 1 shows the detection of a single nucleotide base change by quantification of melting temperatures.

DETAILED DESCRIPTION OF THE PREFERRED EMBODIMENT

Embodiments of the invention concern oligonucleotides that contain universal or generic bases and/or other unnatural bases and methods of using such oligonucleotides to diagnose and treat various diseases.

In some contexts, the term "universal base" is used to describe a moiety that may be substituted for any nucleic acid base. The universal base need not contribute to hybridization, but should not significantly detract from hybridization, whereas "generic bases" are bases that are capable of binding to more than one type of nucleotide. For example a base might be generic for the purine bases or alternatively a base might be generic for the pyrimidine bases. Preferred universal or generic bases include 2-deoxyinosine, 5-nitroindole, 3-nitropyrrole, 2-deoxynebularine, dP, or dK derivatives of natural nucleotides. Some embodiments may also utilize degenerate bases. The term "degenerate base" refers to a moiety that is capable of base-pairing with either any purine, or any pyrimidine, but not both purines and pyrimidines. Exemplary degenerate bases include, but are not limited to, 6H, 8H-3,4-dihydropyrimido[4,5-c][1,2]oxazin-7-one ("P", a pyrimidine mimic) and 2-amino-6-methoxyaminopurine ("K", a purine mimic). In some aspects of the invention, these universal, generic, or degenerate bases are juxtaposed in blocks of artificial bases and in others, they are clustered at either the 5' or 3' end of the oligonucleotide or both. Desirably, at least 2, 3, 4, 5, 6, 7, 8, 9, 10, or 11 universal, generic, or degenerate bases are juxtaposed in each block and an oligonucleotide may contain 1, 2, 3, 4, 5, 6, 7, 8, 9, 10 or 11 blocks depending on the length of the oligonucleotide and the desired effect. Further, some embodiments contain a non-nucleic acid linker such as a spacer 9, spacer 18, spacer C3, or an abasic spacer such as dSpacer so as to provide greater flexibility in the molecule. In some contexts, these spacers are also referred to as universal bases. Preferably, the oligonucleotides described herein are used to increase the efficiency and specificity of existing diagnostic and therapeutic approaches.

It is further contemplated that substituting an unnatural base for a natural base within the oligonucleotide that has a modified affinity, preferably a higher affinity, but a lower affinity may also be used, increases the ability to differentiate a single nucleotide polymorphism or a polymorphic site from a normal site.

As shown herein, the incorporation of universal or generic bases in an oligonucleotide facilitates the differentiation of nucleic acids that differ by as little as a single nucleotide. In fact, it was discovered that the presence of five universal bases decreased the melting temperature of probe-template hybrids by 17° C., as compared to a 6° C. difference when using conventional oligonucleotides. The oligonucleotides of the invention were found to be very specific and exhibit a high affinity for target. By "target" is meant a natural nucleic acid to be detected, quantified, or amplified, etc., consisting of either DNA or RNA, amplified or unamplified and single-stranded or duplex.

Embodiments of the invention include oligonucleotides having at least 20% universal, generic or a mixture of universal and generic bases. Other embodiments include oligonucleotides having at least 21%, 22%, 25%, 30% or 50% universal, generic or a mixture of universal and generic bases. Still more embodiments are oligonucleotides with at least 31%, 32%, 33%, 34%, 35%, 36%, 37%, 38%, 39%, 40%, 45%, 50%, 55%, 60%, or more universal, generic or a mixture of universal and generic bases and unnatural bases located at the SNP position to enhance discrimination. Preferred universal or generic bases are 2-deoxyinosine, 5-nitroindole, 3-nitropyrrole, 2-deoxynebularine, dP, or dK derivatives of natural nucleotides. Some embodiments may also utilize degenerate bases. The term "degenerate base" refers to a moiety that is capable of base-pairing with either any purine, or any pyrimidine, but not both purines and pyrimidines. Exemplary degenerate bases include, but are not limited to, 6H, 8H-3,4-dihydropyrimido[4,5-c][1,2]oxazin-7-one ("P", a pyrimidine mimic) and 2-amino-6-methoxyaminopurine ("K", a purine mimic). In some aspects of the invention, these universal, generic, or degenerate bases are juxtaposed and in others, they are clustered at either the 5' or 3' end of the oligonucleotide or both. Desirably, at least three, four, five, six, seven, or eight universal, generic, or degenerate bases are juxtaposed. Further, some embodiments contain a non-nucleic acid linker such as a spacer 9, spacer 18, spacer C3, or an abasic spacer such as dSpacer and with or without unnatural SNP maximum discrimination base.

The oligonucleotides described herein may also contain natural bases or unnatural base analogs that hydrogen bond to natural bases in the target nucleic acid. Additionally, the oligonucleotides described herein may contain natural bases or unnatural base analogs or other modifications that have a lower affinity to or ability to hydrogen bond to natural bases, relative to any natural base. By "non-naturally occurring base" is meant a base other than A, C, G, T and U, and includes degenerate and universal bases as well as moieties capable of binding specifically to a natural base or to a non-naturally occurring base. Non-naturally occurring bases include, but are not limited to, propynylcytosine, propynyluridine, diaminopurine, 5-methylcytosine, 7-deazaadenosine and 7-deazaguanine. In still more embodiments, the oligonucleotides described above have at least two high affinity domains and one or more low affinity domains.

Embodiments of the invention include oligonucleotides having universal, generic or a mixture of universal and generic bases which are juxtaposed. Preferably, the number of juxtaposed bases is 2 or more. In one embodiment, the number of juxtaposed bases is 4 or more, including but not limited to, 5 or more, 6 or more, 7 or more, and 8 or more. The juxtaposed bases may substitute for any natural base and may substitute for a variety of different natural bases. The juxtaposed bases may be as close as 1 nucleotide from a mismatch or may include the mismatch. Another embodiment concerns a method of increasing the specificity of an oligonucleotide by substituting at least 4 juxtaposed nucleic acids with universal or generic bases. Another embodiment concerns a method of increasing the specificity of an oligonucleotide by substituting at least 5, 6, 7 or more juxtaposed nucleic acids with universal or generic bases.

Embodiments of the invention also include methods of making and using the oligonucleotides described above. For example, one embodiment concerns a method of designing an oligonucleotide, which involves identifying a sequence that corresponds to or complements a target sequence and substituting four or more bases within said sequence with universal or generic bases and with or without unnatural SNP maximum discrimination bases. Another embodiment concerns a method of increasing the specificity of an oligonucleotide by substituting at least 20%, 21%, 22%, 23%, 24%, 25%, 26%, 27%, 28%, 29%, 30%, 31%, 32%, 33%, 34%, 35% or 40% of the total number of bases with universal or generic bases. A further embodiment concerns a method of increasing the specificity of an oligonucleotide by substituting at least 35%, 40%, 45%, 50%, 55%, 60%, or 70% of the total number of bases with universal or generic bases.

The oligonucleotides described herein, though clearly useful for the identification of single nucleotide polymorphisms (SNP's), are also useful for other conventional methods that employ oligonucleotides (e.g., diagnostics, hybridization, sequencing, etc). The oligonucleotides described herein can be used in most methods known to one of skill in the art in which conventional oligonucleotides are used. Although preferred methods concern the use of said oligonucleotides to detect SNPs, embodiments of the invention also encompass the use of said oligonucleotides as primers (e.g., in conjunction with the Taqman™ assay, PCR, or RT-PCR), as probes (e.g., in conjunction with the HPSA™, Molecular Beacon™, HybProbe™, CPT™ and Invader™ assays, northern, Southern, or library hybridizations), in arrays (e.g., chip-based arrays, peptide/nucleic acid virtual arrays, DNA microarrays, antisense scanning arrays, or plate-type arrays) and in other techniques involving oligonucleotides (e.g., 5' or 3' RACE or related techniques). The term "probe" is used herein to mean an oligonucleotide to detect a target nucleic acid, whereas, the term "primer" is used to refer to an oligonucleotide, which can be used to amplify or extend a target nucleic acid. Thus, several embodiments concern diagnostic methods that employ the embodied oligonucleotides in conjunction with a conventional diagnostic technique.

By one approach, a method of detecting the presence or absence of a mutation or polymorphism in a sample comprising nucleic acids is practiced by contacting said nucleic acid with at least one of the oligonucleotides described above, and identifying whether said oligonucleotide binds to said nucleic acid. Preferably, the universal or generic bases of said oligonucleotides are not located at the site or sites of mutation or polymorphism but unnatural bases allowing higher SNP discrimination might be. Additionally, this method can incorporate an amplifying step (e.g., PCR or RT-PCR) to aid in the identification of the presence or absence of the mutation or polymorphism. The section below describes the oligonucleotides of the invention in greater detail.

Oligonucleotides

The oligonucleotides can be of virtually any sequence and of any length, wherein said oligonucleotides comprise at least 20%, 21%, 22%, 23%, 24%, 25%, 26%, 27%, 28%, 29%, 30% or more or up to and including 50% universal or generic bases. The term "oligonucleotide" is used to refer to a molecule consisting of DNA, RNA, or DNA/RNA hybrids with or without non-nucleic acid analogues and polymers. In some embodiments the universal or generic bases are juxtaposed and, in others, clusters of at least two universal or generic bases are sprinkled throughout the oligonucleotide sequence. Preferred sequences correspond to already existing probes, which can be used to identify the presence or absence of a SNP or other genetic marker that has an association with a disease. Preferred sequences, for example, include sequences that indicate a predilection to contract cystic fibrosis (See e.g., U.S. Pat. No. 6,201,107, hereby expressly incorporated by reference in its entirety), sickle cell anemia (See e.g., U.S. Pat. No. 4,683,194, hereby expressly incorporated by reference in its entirety), hemochromatosis (See e.g., U.S. Pat. No. 6,025, 130, hereby expressly incorporated by reference in its entirety), and cancer (See e.g., U.S. Pat. No. 6,194,158, hereby expressly incorporated by reference in its entirety). It should be understood that other sequences known by those of skill in the art, which indicate a predilection to disease can be used to generate the oligonucleotides of the invention.

Oligonucleotide synthesis is well known in the art, as is synthesis of oligonucleotides containing modified bases and backbone linkages. In fact, such oligonucleotides can often be obtained from commercial suppliers upon providing the supplier with the specific sequence and composition information and a request for custom production. Although the preferred length of the oligonucleotides is less than 100 bases, embodiments can be from about 5 to about 500 nucleotides in length, desirably, 10 to about 300 nucleotides in length, more desirably 12 to about 200 nucleotides in length, preferably, 15 to about 100 nucleotides, more preferably 17 to about 50 nucleotides, and most preferably, about 20 to about 40 nucleotides in length.

The oligonucleotides can employ any backbone and any sequence capable of resulting in a molecule that hybridizes to target DNA and/or RNA. Examples of suitable backbones include, but are not limited to, phosphodiesters and deoxyphodiesters, phosphorothioates and deoxyphosphorothioates, 2'-O-substituted phosphodiesters and deoxy analogs, 2'-O-substituted phosphorothioates and deoxy analogs, morpholino, PNA (U.S. Pat. No. 5,539,082, hereby expressly incorporated by reference in its entirety), 2'-O-alkyl methylphosphonates, 3'-amidates, MMI, alkyl ethers (U.S. Pat. No. 5,223,618, hereby expressly incorporated by reference in its entirety) and others as described in U.S. Pat. Nos. 5,378, 825, 5,489,677 and 5,541,307, all of which are hereby expressly incorporated by reference in its entirety. Where RNase activity is desired, a backbone capable of serving as an RNase substrate is employed for at least a portion of the oligonucleotide.

Universal or generic bases suitable for use with the embodiments described herein include, but are not limited to, deoxy 5-nitroindole, deoxy 3-nitropyrrole, deoxy 4-nitrobenzimidazole, deoxy nebularine, deoxyinosine, 2'-Ome inosine, 2'-Ome 5-nitorindole, 2'-Ome 3-nitropyrrole, 2'-F inosine, 2'-F nebularine, 2'-F 5-nitroindole, 2'-F 4-nitrobenzimidazole, 2'-F 3-nitropyrrole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitrobenzimidazole, 2'-O-methoxyethyl 3-nitropyrrole, deoxy $R_pMP$-5-nitroindole dimer 2'-Ome $R_pMP$-5-nitroindole dimer and the like.

Many of the embodied oligonucleotides are characterized in that they share the formula: "XRY", wherein "X" consists of about 5-10, 11-20, or 5-20 modified nucleic acid bases; "R" consists of about 3-5, 6-10, or 3-10 juxtaposed universal or generic bases; and "Y" consists of about 3-5, 6-10, 11-15, or 3-20 nucleic acid bases; wherein X, R, and Y are covalently joined and at least 20%, 21%, 22%, 23%, 24%, 25%, 26%, 27%, 28%, 29%, or 30% or up to and including 50% of the total number of bases are universal or generic bases and X and/or Y might contain a natural or unnatural base at the SNP sight and X and/or Y might contain higher or lower affinity bases or analogues.

Other embodiments include oligonucleotides with the formula: "XRY", wherein "X" consists of about 5-10, 11-20, 21-30, 31-40, 41-50, or 5-50 modified nucleic acid bases or base analogs that have a lower affinity than natural bases; "R" consists of about 3-5, 6-10, 11-15, 16-20, or 3-20 juxtaposed universal or generic bases; and "Y" consists of about 5-10, 11-20, 21-30, 31-40, 41-50, or 5-50 nucleic acid bases; wherein X, R, and Y are covalently joined and at least 20%, 21%, 22%, 23%, 24%, 25%, 26%, 27%, 28%, 29%, or 30% or up to and including 50% of the total number of bases are universal or generic bases.

Still other embodied oligonucleotides have the formula: "XRZRY", wherein "X" consists of about 5-10, 11-20, 21-30, 31-40, 41-50, or 5-50 nucleic acid bases; "R" consists of about 3-5, 6-10, 11-15, 16-20, or 3-20 juxtaposed universal or generic bases; "Z" consists of about 5-10, 11-20, or 5-20 modified nucleic acid bases; and "Y" consists of about 5-10, 11-20, 21-30, 31-40, 41-50, or 5-50 nucleic acid bases; wherein X, R, Z, and Y are covalently joined and at least 20%, 21%, 22%, 23%, 24%, 25%, 26%, 27%, 28%, 29%, or 30% or up to and including 50% of the total number of bases are universal or generic bases.

Still other embodied oligonucleotides have the formula: "XZRZY", wherein "X" consists of about 5-10, 11-20, 21-30, 31-40, 41-50, or 5-50 nucleic acid bases; "R" consists of about 3-5, 6-10, 11-15, 16-20, or 3-20 juxtaposed universal or generic bases; "Z" consists of about 5-10, 11-20, or 5-20 modified nucleic acid bases, which have a lower or higher affinity than natural bases; and "Y" consists of about 5-10, 11-20, 21-30, 31-40, 41-50, or 5-50 nucleic acid bases; wherein X, R, Z, and Y are covalently joined and at least 20%, 21%, 22%, 23%, 24%, 25%, 26%, 27%, 28%, 29%, or 30% or up to and including 50%, of the total number of bases are universal or generic bases.

More embodied oligonucleotides have the formula: "XZXRXZX", wherein "X" consists of about 5-10, 11-20, 21-30, 31-40, 41-50, or 5-50 nucleic acid bases; "R" consists of about 3-5, 6-10, 11-15, 16-20, or 3-20 juxtaposed universal or generic bases; "Z" consists of about 5-10, 11-20, or 5-20 modified nucleic acid bases, which have a lower or higher affinity compared to natural bases; wherein X, R, and Z are covalently joined and at least 20%, 21%, 22%, 23%, 24%, 25%, 26%, 27%, 28%, 29%, or 30% or up to and including 50% of the total number of bases are universal or generic bases.

Still more embodied oligonucleotides have the formula: "YXZXRY", wherein "X" consists of about 5-10, 11-20, 21-30, 31-40, 41-50, or 5-50 nucleic acid bases; "R" consists of about 3-5, 6-10, 11-15, 16-20, or 3-20 juxtaposed universal or generic bases; "Z" consists of about 5-10, 11-20, or 5-20 modified nucleic acid bases, which have a lower or higher affinity than natural bases; and "Y" consists of about 5-10, 11-20, 21-30, 31-40, 41-50, or 5-50 nucleic acid bases; wherein X, R, Z, and Y are covalently joined, at least two nucleotides of Y are covalently linked by a non-nucleic acid linker, and at least 20%, 21%, 22%, 23%, 24%, 25%, 26%, 27%, 28%, 29%, or 30% or up to and including 50% of the total number of bases are universal or generic bases.

The oligonucleotides described herein can be sold separately or can be incorporated in kits that facilitate genetic analysis. For example, many SNP diagnostic kits are currently available. These kits typically provide oligonucleotide primers, which are to be used to detect a specific SNP that is associated with a disease. Aspects of the invention include diagnostic kits comprising probes and primers that are manufactured in accordance with the oligonucleotide structures described herein. That is, embodiments of the invention include diagnostic kits comprising an oligonucleotide, wherein at least 20%, 21%, 22%, 23%, 24%, 25%, 26%, 27%, 28%, 29%, or 30% or up to and including 50% of the total number of bases of said oligonucleotide are universal or generic bases and may or may not contain other unnatural bases. The kits may optionally provide a support (e.g., nitrocellulose, nylon, plastic, or other macromolecule) hybridization or amplification reagents, and instructions. The section below describes in greater detail many of the methods concerning the oligonucleotides described herein.

Methods

Embodiments of the invention also include methods of making and using the oligonucleotides described above. One embodiment concerns a method of designing an oligonucleotide, which involves identifying a sequence that corresponds to or complements a target sequence and substituting sufficient bases within said sequence with universal or generic bases so as to achieve an overall composition in which at least 20%, 21%, 22%, 23%, 24%, 25%, 26%, 27%, 28%, 29%, or 30% or up to and including 50% of the total number of bases are universal or generic bases. By one approach, a sequence that interacts with a target that indicates the presence or absence of a disease is selected from U.S. Pat. No. 6,201,107; 4,683,194; 6,025,130; or 6,194,158 (all of which are hereby expressly incorporated by reference in their entireties) and at least 20%, 21%, 22%, 23%, 24%, 25%, 26%, 27%, 28%, 29%, or 30% of the total number of bases are swapped with universal or generic bases. Preferably, all of the universal bases are juxtaposed or are clustered at either the 5' or 3' end of the oligonucleotide. Care should be taken such that the diagnostic site (e.g., site of the SNP or mutation) is not covered by the universal bases, but may be covered by an unnatural base to enhance SNP discrimination. That is, preferably, the diagnostic site is complemented by a natural base and the stretch of universal or generic bases are positioned such that an optimal difference in melting behavior between the polymorphic/probe complex and non-polymorphic target/probe complex is achieved.

The oligonucleotides described herein, though clearly useful for the identification of single nucleotide polymorphisms (SNP's), are also useful for other conventional methods that employ oligonucleotides (e.g., diagnostics, hybridization, sequencing, etc). The oligonucleotides described herein can be used in most methods known to one of skill in the art in which conventional oligonucleotides are used.

Thus, the oligonucleotides described herein are useful for the identification of any mutations, allelic variants, polymorphisms, and the normal or wild-type sequence of a gene. In addition, the oligonucleotides described herein may be used to detect the presence of a sequence, or alternatively, the oligonucleotides may be used to identify the amount of a particular mRNA with is being produced by a cell. The quantitation may be in addition to, or separately from the identification of the presence.

However, because the most common type of human genetic variation is the single-nucleotide polymorphism (SNP), a base position at which two alternative bases occur at appreciable frequency (>1%) in the population, the utilization of SNPs for clinical diagnostics, whole-genome linkage disequilibrium screens, determination of the recent evolutionary history of a species, and the process of speciation has become a major focus of human genetics. Thus, methods of genotyping or determining the presence or absence of a mutation or polymorphism, preferably a SNP, using the oligonucleotides described herein are extremely useful embodiments.

A prototypical example of the forthcoming primary public health role of molecular diagnostics (particularly of SNPs) is the identification of individuals affected by or at-risk for the iron overload disorder hereditary hemochromatosis. More than 90% of the cases of this most common of all single-gene disorders (present in 0.5% of whites) are caused by the presence of a homozygous well-conserved single nucleotide substitution (nucleotide G845A; amino acid C282Y) in the transferrin receptor binding protein HFE. This loss-of-function mutation abolishes HFE's usual cell surface expression, thus preventing its ability to down-regulate the affinity of transferrin receptor for transferrin-bound iron.

The result is a dysregulation of normal cellular iron metabolism and a resulting constitutive intestinal iron absorption. This excess toxic iron deposits in numerous organs and, if not removed, causes progressive chronic damage to the liver, heart, endocrine glands, joints, and skin. Because hemochromatosis is a common, underdiagnosed (but easily diagnosable), progressive chronic disease with late-onset symptomotology for which an effective, safe (preventative) therapy is widely available (phlebotomy), it is perhaps the ideal disease for the implementation of a population-based screening program.

Universal population-based hemochromatosis screening by transferrin saturation has been recommended by the College of American Pathologists, and a more conservative phenotypic screening of "symptomatic" individuals has been recommended by an expert consensus panel of the Centers for Disease Control (CDC) and the National Institutes of Health (NIH). More universal recommendations for widespread population screens may result from the recently initiated NIH study (HEIRS) of 100 000 apparently healthy Americans that will evaluate the benefits and risks of iron overload screening by both genotypic and phenotypic determinations. Therefore, the need to identify this SNP and diagnose this debilitating disease early on is manifest.

Accordingly, an individual at risk for hemochromatosis can be identified by selecting probes or primers that allow for the detection of the well-conserved single nucleotide substitution, nucleotide G845A. (See e.g., U.S. Pat. No. 6,025,130, hereby expressly incorporated by reference in its entirety, wherein specific primers and probes can be obtained). Once suitable primers are selected they can be designed to have a sufficient amount of universal or generic bases to allow for optimal melting behavior discrimination. The oligonucleotides having universal or generic bases can then be used to identify whether said individual has the mutation that indicates the disease.

In a similar fashion, an individual at risk for cystic fibrosis (CF) can be identified (suitable primers or probes are identified in U.S. Pat. No. 6,201,107), an individual at risk of contracting cancer can be identified (suitable primers and probes are identified in U.S. Pat. No. 6,194,158, hereby expressly incorporated by reference in its entirety), and an individual at risk for sickle cell anemia can be identified (suitable primers and probes are identified in U.S. Pat. No. 4,683,194, hereby expressly incorporated by reference in its entirety).

Although some preferred methods concern the use of said oligonucleotides to detect SNPs, the embodied oligonucleotides can also be used as primers (e.g., in conjunction with the Taqman™ assay, PCR, or RT-PCR), as probes (e.g., in conjunction with the HybProbe™, CPT™ and Invader™ assays, northern, Southern, or library hybridizations), in arrays (e.g., chip-based arrays, peptide/nucleic acid virtual arrays, DNA microarrays, antisense scanning arrays, or plate-type arrays) and in other techniques involving oligonucleotides (e.g., 5' or 3' RACE or related techniques).

The following examples describe in greater detail techniques that can be used to make the oligonucleotides described herein.

EXAMPLE 1

By one approach, the oligonucleotides described herein were made using a Perkin-Elmer Applied Biosystems Expedite synthesizer. All reagents were used dry (<30 ppm water) and the oligonucleotide synthesis reagents were purchased from Glen Research. Amidites of normal bases, or universal bases, in solution were dried over Trap-paks (Perkin-Elmer Applied Biosystems, Norwalk, Conn.). A solid support previously derivatized with a dimethoxy trityl (DMT) group protected propyl linker was placed in a DNA synthesizer column compatible with a Perkin-Elmer Applied Biosystems Expedite synthesizer (1 mmol of starting propyl linker). The DMT group was removed with a deblock reagent (2.5% dichloroacetic acid in dichloromethane). The standard protocols for RNA and DNA synthesis were applied to the amidites (0.1 M in dry acetonitrile). The amidites were activated with tetrazole (0.45 M in dry acetonitrile). Coupling times were typically up to 15 minutes depending on the amidite. The phosphonite intermediate was treated with an oxidizing Beaucage sulfurizing reagent.

After each oxidation step, a capping step was performed, which places an acetyl group on any remaining uncoupled 5'-OH groups by treatment with a mixture of two capping reagents: CAP A (acetic anhydride) and CAP B (n-methylimidazole in THF). The cycle was repeated a sufficient number of times with various amidites to obtain the desired oligonucleotide sequence.

Once the desired sequence was obtained, the support was treated at 55° C. in concentrated ammonium hydroxide for 16 hours. The solution was concentrated on a speed vac and the residue was taken up in 100 ml aqueous 0.1 ml triethylammonium acetate. This material was then applied to an HPLC column (C-18, Kromasil, 5 mm, 4.3 mm diameter, 250 mm length) and eluted with an acetonitrile gradient (solvent A, 0.1 M TEAA; solvent B, 0.1 M TEAA and 50% acetonitrile) over 30 minutes at 1 ml/min flow rat. Fractions containing greater than 80% pure product are pooled and concentrated. The resulting residue was taken up in 80% acetic acid in water to remove the trityl group and reapplied to a reverse phase column and purified as described above. Fractions containing greater than 90% purity were pooled and concentrated. By following the approach described above with modifications that are apparent to one of skill in the art, the oligonucleotides described herein can be made, isolated, and purified. The following example describes several preferred structures for designing the embodied oligonucleotides.

EXAMPLE 2

Several motifs that facilitate the identification of SNPs were discovered and this example describes these structures in greater detail. The oligonucleotide motifs are described using the following letter identifications:

N=Natural bases or unnatural base analogues in the oligonucleotide that hydrogen bond to natural bases in the target nucleic acid. N may be higher or lower affinity than natural bases due to base, sugar, backbone, or any other non-nucleic acid modifications or structures, (e.g. peptide nucleic acids).

S=Natural bases or unnatural base analogs or other modification that has a lower affinity to or ability to hydrogen bond to natural bases, relative to any natural base. These bases can stack in the duplex, but have lower affinity to specific opposing natural bases.

B=Any "Universal" or "generic" base analogues or other modification that can stack in duplex nucleic acid helices but do not significantly discriminate among opposing natural bases (universal, e.g. 2-deoxyinosine, 5-nitroindole, 3-nitropyrrole, 2-deoxynebularine) or that have a reduced ability to discriminate among opposing natural bases (generic, e.g. dP or dK).

X=Natural base or unnatural base substitution or any other modification within the oligonucleotide that increases the negative impact of a mismatch against the target nucleic acid. X can occur in any region of the oligonucleotide.

L=Non-nucleic acid linker (e.g. Spacer 9, Spacer 18, Spacer C3, dSpacer, all from Glen Research) either as a base substitution or contained between any pair of bases in the probe.

Representative classes of oligonucleotides for use with many of the embodiments described herein are shown below.

```
        (  1  )(  2  )(  3  )
1.      NNNNNNNBBBBBNNNNNNN (  1  )(  2  )(  3  )
2.      NNNLNNNBBBBBNNNNNNN (  1  )(  2  )(  3  )
3.      NNNNNNNLBBBBBNNNNNNN (  1  )(  2  )(  3  )
4.      NNNNNNLBBBBBBLNNNNNN (  1  )(  2  )(  3  )
5.      NNNNNNNBBBBBBNNNLNN ( 1 )(2)(3)(4)( 5 )
6.      NNNNNBBBNNNBBBNNNNN
```

TABLE 1 describes the unnatural and natural base choices that allow one to 1) discriminate SNP bases more precisely that natural bases alone, and 2) create the higher and lower affinity blocks included in the oligonucleotides of the preferred embodiment.

TABLE 1

| Natural Base | NATURAL BASE TO AVOID BINDING | | | |
|---|---|---|---|---|
| | G | A | T | C |
| G | — | *N4-Et-dC | dC | dC |
| | — | ##not 5-Me-dC | 5-Me-dC | 5-Me-dC |
| | — | ##not dC | | |
| A | 2-Thio-dT | — | 2-Thio-dT | 2-Thio-dT |
| | not dT | — | | |
| T | **2-amino-dA | 2-amino-dA | — | 2-amino-P |
| | not dA | — | | #not 2-amino-dA |
| | | — | | #not dA |
| C | dG | ***dX | dX | — |
| | | not dG | not dG | — |
| | | | | — |

Relative binding strength estimates contributing to choices:
*5-Me-dC: dG > dC: dG > N4-Et-dC: dG? > ?N4-Et-dC: dA
dT: dA = 5MedC: dA > dC: dA = dU: dA
**2-amino-dA: dT > dA: dT >> 2-amino-dA: dG
***dX: dC = dA: dU >> dX: dG < dA: dG = dA: dI
2-amino-dA: dC > dA: dC = dA: dU >> dA: dI It is further contemplated that placing an unnatural base that has a modified affinity, preferably a higher affinity, but a lower affinity may also be used, increases the ability to differentiate a single nucleotide polymorphism or a polymorphic site from a normal site.

Table 1 shown above is designed to exemplify the way any natural or unnatural base or analogue can be selected to maximize SNP discrimination in combination with universal or generic bases. Given any of the general structure permutations shown above (numbered 1-6), for any SNP in any position, Table 1 allows one to determine which base to use for the specific SNP base. For example, it can be used to determine which base one wants this probe to bind to in the target versus the SNP base in the non-target. Most wild-type versus mutant SNP detection systems have both wild-type and mutant targets in the mixture, so one has to absolutely maximize the ability to discriminate the two SNP bases that define wild-type versus mutant and the Table allows one to do so. If one were trying to get better discrimination between an adenine in the wt target and guanine in the mutant target (the SNP), one could go to the table and look up "adenine" as the natural base and under the heading "guanine", one finds "2-Thio-dT" which tells you that you will get the best discrimination between "A" and "G" if "2-Thio-dT" is used in the primer. This is further illustrated in Examples 12 and 13.

The next example illustrates that the incorporation of universal or generic bases in an oligonucleotide facilitates the differentiation of two sequences that differ by a single nucleotide.

EXAMPLE 3

In these experiments it was demonstrated that oligonucleotides having universal bases facilitate the identification of a single nucleotide base change in a nucleic acid. In a first set of experiments, the differences in melting behaviors of a natural probe/target complex and an oligonucleotide probe having 5 universal bases/target complex was ascertained. The mutant target contained a single mismatch, a G - - G mismatch to both probes, OGC2 and OGX2.

As shown in FIG. 1, the all-natural probe OGC2 (SEQ ID NO: 2) bound to the mismatch target #1090 (SEQ ID NO: 8) with a differential melting temperature of −6° C. relative to the perfect match wild-type target #1088 (SEQ ID NO: 7). OGX2 (SEQ ID NO: 4), the oligonucleotide containing 5 universal bases, bound with a differential melting temperature of −17° C. relative to the perfect match. The slight difference of −6° C. in melting temperature using the control probe (OGC2) is undetectable using most diagnostic methods. In the presence of five universal bases, however, the single purine-purine mismatch decreases the perfect-probe-to-target melting temperature by 17° C., thereby facilitating the specific detection of the SNP in the target oligonucleotide.

Multiple melting temperature determinations were performed for each probe/target combination. All mixtures were heated to 85-95° C. for 10-15 minutes and allowed to cool to room temperature before use. Melting temperatures were determined by UV absorbence in sealed quartz cuvettes using a Varian Cary 3E UV-Visible Spectrophotometer with a Varian Cary temperature controller, controlled with Cary 01.01(4) Thermal software. Temperature gradients decreased from 85° C. to 25° C. at 1° C. per minute. The following example details experiments that examined the effect of salt concentration on the oligonucleotides described herein.

EXAMPLE 4

Melting temperatures were determined for the following three probes containing generic and universal bases in various salt concentrations and the results were compared to those obtained using a control probe without the generic and universal bases (5' natural OGC2). The probes analyzed included 5' OGX1 (SEQ ID NO: 3), 5'OGX3 (SEQ ID NO: 5), 5' OGX5 (SEQ ID NO: 6) and 5' natural OGC2 (SEQ ID NO: 2). The target was #1088 (SEQ ID NO: 7). Oligonucleotide probes and DNA targets were at 0.35 to 0.40 O.D. each per milliliter in both an enzymatically relevant buffer system (KCl/Mg++) or in a non-physiological, high salt buffer system (NaCl/PO$_4$−−):

| KCl/Mg++ Buffer: | NaCl/PO$_4$-- Buffer: |
|---|---|
| 20 mM Tris-HCl, pH = 7.5 at 20° C. | 10 mM NaH$_2$PO$_4$, pH = 7.0 at 20° C. |
| 100 mM KCl | 1 M NaCl |
| 10 mM MgCl$_2$ | 0.1 EDTA |
| 0.05 mM DTT | |
| 2.5% w/v sucrose | |

Multiple melting temperature determinations were performed for each probe/target combination. All mixtures were heated to 85-95° C. for 10-15 minutes and allowed to cool to room temperature before use. Melting temperatures were determined by UV absorbence in sealed quartz cuvettes using a Varian Cary 3E UV-Visible Spectrophotometer with a Varian Cary temperature controller, controlled with Cary 01.01(4) Thermal software. Temperature gradients decreased from 85° C. to 25° C. at 1° C. per minute.

As shown in TABLE 2, the difference in melting behavior of oligonucleotides having universal or generic bases and natural oligonucleotides were not influenced by salt concentration.

TABLE 2

| | KCl/Mg++ | | NaCl/PO$_4$-- | |
|---|---|---|---|---|
| Probe | Match T$_M$ | MisMatch T$_M$ | Match T$_M$ | MisMatch T$_M$ |
| 5' OGX1 | <25 | 53 | <25 | 58 |
| 5' OGX3 | <25 | 51 | <25 | 57 |
| 5' OGX5 | <25 | 56 | <25 | 63 |
| 5' natural OGC2 | 64 | 70 | 71 | 75 |

The following example demonstrates that the oligonucleotides described herein can be used to detect single base changes in polyacrylamide gel electrophoresis detection systems.

EXAMPLE 5

The melting behavior of control probes (i.e., no universal and generic bases) OGC1 (SEQ ID NO: 1) and OGC2 (SEQ ID NO: 2) annealed to two different target DNA's: #1088 (SEQ ID NO: 7), which contains a G to C match, and #1090 (SEQ ID NO: 8), which contains a G-G mismatch, were compared to the melting behaviors of probes containing universal and generic bases. The universal or generic base containing probes analyzed included 5' OGX1 (SEQ ID NO: 3), 5'OGX2 (SEQ ID NO: 4), and 5' OGX5 (SEQ ID NO: 6).

A polyacrylamide gel bandshift experiment was then conducted as follows. The gel matrix was 20% acrylamide (19:1 acrylamide to bis-acrylamide) in 1×TBE buffer and "extra" salts: 20 mM Tris-HCl, pH=7.5 at 20° C., 100 mM KCl, 10 mM MgCl$_2$, 0.05 mM DTT, 2.5% w/v sucrose. Oligonucleotide mixtures were at approximately 5 micromolar each in formamide/dye sample buffer plus 2× of the extra salt concentrations in the acrylamide gel mixture. The gel was run in 1×TBE at 93V (19 mA) and the buffer and gel temperatures were kept stable at 26° C. during the entire electrophoretic run.

The polyacrylamide gel was scanned, lanes 1-12, and the oligonucleotide probe/DNA target sequences were analyzed. Probe and DNA target designations are provided in TABLE 3. Lanes 11 and 12 of the gel marked the position of unbound target DNAs (#1088, perfect match and #1090, single base mismatch, respectively).

Lanes 1, 2, 3, and 4 of the gel showed that the all-natural-base probes (OGC1 and OGC2) could not distinguish the single base mismatch target (#1090, lanes 2 and 4) from the perfectly matched target (#1088, lanes 1 and 3). Lanes 5 through 10, on the other hand, graphically revealed the ability of the probes containing juxtaposed universal bases to detect a single-base-mismatch under these conditions. Thus, the results above provide more evidence that antisense oligonucleotides comprising juxtaposed universal bases are more specific for a target than conventional oligonucleotides, which translates into improved antisense inhibition.

TABLE 3

| | Size | Name | Identity |
|---|---|---|---|
| Control Oligonucleotides: | | | |
| 5' ctGctaactgagcacAggatg (C6-NH2) | 21 mer | OGC1 (SEQ ID NO: 1) | control |
| 5' gagctGctaactgagcacAgg (C6-NH2) | 21 mer | OGC2 (SEQ ID NO: 2) | control |
| Experimental Oligonucleotides | | | |
| 5' ctGctaBBBBBgcacAggatg (C6-NH2) | 21 mer | OGX1 (SEQ ID NO: 3) | 6/5/10 |
| 5' gagctGctaaBBBBBcacAgg (C6-NH2) | 21 mer | OGX2 (SEQ ID NO: 4) | 10/5/6 |
| 5' gctGctaBBBBBgcacAgg (C6-NH2) | 19 mer | OGX3 (SEQ ID NO: 5) | |
| 5' gagctGctBBBBBagcacAgg (C6-NH2) | 21 mer | OGX5 (SEQ ID NO: 6) | 8/5/8 |
| Target DNA's | | | |
| 3' tactcgaCgattgactcgtgTcctactggaccctggg | #1088 | Target (SEQ ID NO: 7) | 37 mer |

TABLE 3-continued

| | Size | Name | Identity |
|---|---|---|---|
| 3' tactcgaGgattgactcgtgTcctactggaccctggg | #1090 | Target (SEQ ID NO: 8) | 37 mer |

The next example demonstrates that oligonucleotides that have a total base composition of greater than 20% universal or generic bases, wherein two or more of the universal or generic bases are in a juxtaposed position, facilitate the identification of a single base mismatch on a target, as compared to oligonucleotides having a total base composition that is less than 20% and/or no juxtaposed universal or generic bases.

EXAMPLE 6

This example provides evidence that the oligonucleotides described herein unexpectedly facilitate the identification of mutations or polymorphisms, as compared to other types of oligonucleotides, which may have universal or generic bases that are not juxtaposed. Melting behavior experiments are performed to analyze the melting behaviors of oligonucleotides that have a universal or generic base composition that is greater than or less than 20% of the total base composition. Additionally, the melting behavior effect of the universal or generic bases in a juxtaposed or non-juxtaposed position is also analyzed.

The melting temperature determinations were performed for each probe/target combination as above. All mixtures were heated to 85-95° C. for 10-15 minutes and allowed to cool to room temperature before use. Melting temperatures were determined by UV absorbence in sealed quartz cuvettes using a Varian Cary 3E UV-Visible Spectrophotometer with a Varian Cary temperature controller, controlled with Cary 01.01(4) Thermal software. Temperature gradients were decreased from 85° C. to 25° C. at 1° C. per minute.

The following oligonucleotides were analyzed: The improved probes (#3192-3187) contained increasing numbers of 5-nitroindole substitutions (B). These were compared to an all-natural base probe (3179) for the ability to distinguish between a wild-type target (3221) and a mutant target containing a single SNP (3222). Probe/target melting temperatures were estimated by thermal denaturation profiles according to previously described methods. The results revealed that a single unnatural base substitution offers lower discrimination than larger numbers of substitutions, and that unnatural base substitutions can be very effective immediately adjacent to the SNP position. See Table 4:

TABLE 4

| Probe | | Tm Wild Type 3211 Tm ° C. | Tm Mutant 3222 Tm ° C. | Delta Tm ° C. |
|---|---|---|---|---|
| 3179 | Tacgtgccaggtggagcacccag (SEQ ID NO: 8) | 82.1 | 77.2 | 4.9 |
| 3192 | TacgtgccaggBggagcacccag (SEQ ID NO: 9) | 79.3 | 73.8 | 5.5 |
| 3191 | tacgtgccagBBBgagcacccag (SEQ ID NO: 10) | 74.7 | 68.8 | 5.9 |
| 3190 | tacgtgccaBBBBBagcacccag (SEQ ID NO: 11) | 66.0 | 57.1 | 8.9 |
| 3189 | tacgtgccBBBBBBBgcacccag (SEQ ID NO: 12) | 59.3 | 44.8 | 14.5 |
| 3188 | tacgtgcBBBBBBBBBcacccag (SEQ ID NO: 13) | 64.6 | 52.0 | 12.6 |
| 3187 | tacgtgBBBBBBBBBBacccag (SEQ ID NO: 14) | 66.5 | 54.5 | 12.0 |
| 3221 | 5' gcctgggtgctccacctggcacgtatatc 3' (SEQ ID NO: 15) | | Wild Type "C" target | |
| 3222 | 5' gcctgggtgctccacctggtacgtatatc 3' (SEQ ID NO: 16) | | Mutation "T" target | |

Further oligonucleotides are analyzed as follows: the "Z" represents a 3-nitropyrrole at the indicated position, "G" indicates the polymorphism on TARGETS A and B, and TARGET C does not have a polymorphism. Oligonucleotides 1-4 and TARGETS A, B, and C are described in U.S. Pat. No. 5,780,233 to Guo et al., herein expressly incorporated by reference in its entirety.

(1)
5' CTCTTGAGAGAGCTAGTATCT 3'   (SEQ ID NO: 17)

-continued

```
(2)
5' CTCTTGZGAGAGCTZGTATCT 3'      (SEQ ID NO: 18)

(3)
5' CTCTTZAGAGAGCTAZTATCT 3'      (SEQ ID NO: 19)

(4)
5' CTCTZGAGAGAGCTAGZATCT 3'      (SEQ ID NO: 20)

(5)
5' CTCTZZAGAGAGCTAZZZTCT 3'      (SEQ ID NO: 21)

(6)
5' CTCTZZZGAGAGCTAZZATCT 3'      (SEQ ID NO: 22)

(7)
5' CTCTTGAGAGAGCZZZZZTCT 3'      (SEQ ID NO: 23)

(8)
5' CTCZZZZZAGAGCTAGTATCT 3'      (SEQ ID NO: 24)

(9)
5' CTCZZZZZAGAGCZZGTATCT 3'      (SEQ ID NO: 25)

(10)
5' CTCZZZZZGAGAGCZZZTATCT 3'     (SEQ ID NO: 26)

(TARGET A)
AGATACTAGCGCTCTCAAGAG            (SEQ ID NO: 27)

(TARGET B)
AGATACTAGCTCGCTCAAGAG            (SEQ ID NO: 28)

(TARGET C)
AGATACTAGCTCTCTCAAGAG            (SEQ ID NO: 29)
```

The results will show that oligonucleotides, which have a universal or generic base composition that is greater than 20%, wherein said universal or generic bases are juxtaposed, melt from TARGETS A and B at a lower temperature than the other oligonucleotides (i.e., oligonucleotides 1-4).

The next example also demonstrates that oligonucleotides that have a total base composition of greater than 20% universal or generic bases, wherein two or more of the universal or generic bases are in a juxtaposed position, facilitate the identification of a single base mismatch on a target, as compared to oligonucleotides having a total base composition that is less than 20% and/or no juxtaposed universal or generic bases.

EXAMPLE 7

This example provides evidence that the oligonucleotides described herein facilitate the identification of mutations or polymorphisms, as compared to other types of oligonucleotides, which may have universal or generic bases that are not juxtaposed. In brief, a polyacrylamide gel band shift experiment is performed to analyze the melting behaviors of oligonucleotides that have a universal or generic base composition that is greater than or less than 20% of the total base composition. Additionally, the melting behavior effect of the universal or generic bases in a juxtaposed or non-juxtaposed position is also analyzed.

The polyacrylamide gel bandshift experiment is conducted as above. The gel matrix is 20% acrylamide (19:1 acrylamide to bis-acrylamide) in 1×TBE buffer and "extra" salts: 20 mM Tris-HCl, pH=7.5 at 20° C., 100 mM KCl, 10 mM MgCl$_2$, 0.05 mM DTT, 2.5% w/v sucrose. Oligonucleotide mixtures are at approximately 5 micromolar each in formamide/dye sample buffer plus 2× of the extra salt concentrations in the acrylamide gel mixture. The gel is run in 1×TBE at 93V (19 mA) and the buffer and gel temperatures are kept stable at 26° C. during the entire electrophoretic run.

The following oligonucleotides are analyzed; the "Z" represents a 3-nitropyrrole at the indicated position, "G" indicates the polymorphism on TARGETS A and B, and TARGET C does not have a polymorphism. Oligonucleotides 1-4 and TARGETS A, B, and C are described in U.S. Pat. No. 5,780,233 to Guo et al., herein expressly incorporated by reference in its entirety.

```
(1)
5' CTCTTGAGAGAGCTAGTATCT 3'      (SEQ ID NO: 30)

(2)
5' CTCTTGZGAGAGCTZGTATCT 3'      (SEQ ID NO: 31)

(3)
5' CTCTTZAGAGAGCTAZTATCT 3'      (SEQ ID NO: 32)

(4)
5' CTCTZGAGAGAGCTAGZATCT 3'      (SEQ ID NO: 33)

(5)
5' CTCTZZAGAGAGCTAZZZTCT 3'      (SEQ ID NO: 34)

(6)
5' CTCTZZZGAGAGCTAZZATCT 3'      (SEQ ID NO: 35)

(7)
5' CTCTTGAGAGAGCZZZZZTCT 3'      (SEQ ID NO: 36)

(8)
5' CTCZZZZZAGAGCTAGTATCT 3'      (SEQ ID NO: 37)

(9)
5' CTCZZZZZAGAGCZZGTATCT 3'      (SEQ ID NO: 38)

(10)
5' CTCZZZZZGAGAGCZZZTATCT 3'     (SEQ ID NO: 39)

(TARGET A)
AGATACTAGCGCTCTCAAGAG            (SEQ ID NO: 40)

(TARGET B)
AGATACTAGCTCGCTCAAGAG            (SEQ ID NO: 41)

(TARGET C)
AGATACTAGCTCTCTCAAGAG            (SEQ ID NO: 42)
```

The gel will reveal that oligonucleotides, which have a universal or generic base composition that is greater than 20%, wherein said universal or generic bases are juxtaposed, facilitate the identification of the mismatch in TARGETS A and B, as compared to the other oligonucleotides (i.e., oligonucleotides 1-4).

The next example describes the use of the oligonucleotides described herein in conjunction with the Taqman™ assay to identify a SNP associated with Hereditary hemochromatosis.

EXAMPLE 8

Taqman™ probes derive their fluorescence signal from the hydrolysis of the probe by Taq's 5' to 3' exonuclease activity. The hydrolysis separates fluorescein from a quenching dye and results in an increased fluorescein signal. These probes can be used in the LightCycler™ and are monitored in F1 or F1/F2. In the following assay, the C282Y mutation in the Hereditary hemochromatosis (HH) gene (HFE) is assayed using dried blood spots from a number of neonatal samples of dried blood.

The C282Y mutation is determined by the TaqMan™ technology, which is based on the use of two fluorescent dyes (a reporter and a quencher), both attached to the probe. During PCR, the probe anneals to the target sequence between the forward and the reverse primer sites. If hybridization occurs, the probe is cleaved by the 5'-nuclease activity of the polymerase. This separates the reporter from the quencher, generating an increase in the reporter's fluorescence. Differences in fluorescence facilitate discrimination of all HFE genotypes at the 282 position. The Taqman™ method is described in Kazuko, et al. U.S. Pat. No. 5,952,202, issued Sep. 14, 1999 (herein expressly incorporated by reference in its entirety).

PCR is performed by amplifying 100-500 ng of genomic DNA in a 50-μl volume using the TaqMan PCR Core Reagent Kit reagents (PE Applied Biosystems, Foster City, Calif.). The following conditions are used: 8% (vol/vol) glycerol, 1× TaqMan buffer, 5 mM MgCl$_2$, 200 μM dNTP mix, 300 nM of both primers, 200 nM of normal probe, 50 nM of mutated probe, 0.01 U/μl Amp Erase UNG, and 0.05 U.μl AmpliTaq Gold. However, primers are modified, as disclosed above, for comparison.

After an incubation of 2 min at 50° C. for optimal activity of AmpErase Uracil-N-Glycosylase, and an incubation of 10 min. at 95° C. to activate AmpliTaq Gold, the following cycling protocol is run: 40 cycles of denaturation at 95° C. for 15 sec, then annealing and extension at 64° C. for 1 min. Reactions are performed in an ABI Prism 7700 Sequence Detection System (PE Applied Biosystems, Foster City, Calif.). Fluorescence is measured directly in the closed tubes. Also included in the assay are control reactions containing no template, known allele:template 1 (homozygous mutant), and known allele:template 2 (homozygous normal).

The primers modified as in the preferred embodiments described herein are able to identify the mismatch with a much lower number of false negatives and false positives than conventional probes. Accordingly, the embodiments described herein facilitate the discrimination of an SNP using the Taqman™ assay. The next example describes the use of the oligonucleotides described herein in conjunction with the HybProbe™ assay to identify a SNP associated with vascular disease.

EXAMPLE 9

The HybProbe™ assay is also called a two-color melting curve assay. HybProbe™ chemistry consists in two adjacent probes in a head-to-tail orientation, spaced by one to four nucleotides. The probes hybridize to adjacent sequences. One of the probes is labeled at its 3' end by a donor dye (generally flurescein). The other probe is labeled with an acceptor molecule at its 5' end (generally LC Red640 or 705), and is phosphate-blocked at the 3' end. When both probes are hybridized to their target sequences, the emitted light of the donor is transmitted to the acceptor fluorophore by Förster resonance energy transfer (FRET), and the Red640 emitted fluorescence (640 nm) can be detected. The intensity of the emitted fluorescence increases in parallel with the target DNA formed in the PCR. The LightCycler probes offer the advantage over the TaqMan™ probe of not requiring hydrolysis and, therefore, no additional extension of the PCR times (annealing-elongation≦12 s). A method such as that in US patent applications: Wittwer et al. U.S. Pat. No. 6,232,079, issued May 15, 2001 and Wittwer et al. U.S. Pat. No. 6,140,054, issued Oct. 31, 2000 (both of which are herein incorporated by reference in their entireties) is used.

Similar to the experiments described in example 7 of the Wittwer et al. U.S. Pat. No. 6,232,079, issued May 15, 2001, the MTHFR SNP can be detected with the primers of the preferred embodiment in conjunction with a typical HybProbe™ assay. There is a common point mutation in the methylenetetrahydrofolate reductase (MTHFR) gene (C.sub.677 T) that converts an alanine to a valine residue and results in a thermolabile enzyme. This mutation can reduce MTHFR activity and lead to elevated homocysteine plasma levels which has been implicated as an independent risk factor for early vascular disease and thrombosis as is well known in the art.

Accordingly, one of the primers is labeled with Cy5 (TGAAGGAGAAGGTGTCT*GCGGGA) (SEQ ID NO: 43) where T* represents a modified T residue linked to Cy5. The probe sequence is fluorescein-CCTCGGCTAAATAG-TAGTGCGTCGA (SEQ ID NO: 44) and the other primer is AGGACGGTGCGGTGAGAGTG (SEQ ID NO: 45). Two primers and a probe are developed to conform to the primers of the preferred embodiment by making variations of SEQ ID NOS: 43 and 45.

A 198 base pair fragment of the MTHFR gene is amplified from 50 ng of human genomic DNA in 50 mM Tris, pH 8.3, 2 mM MgCl$_2$, 500 μg/ml bovine serum albumin, 0.2 mM of each dNTP, 0.5 μM of the Cy5-labeled primer, 0.1 μM of the opposing primer, 0.1 μM of the fluorescein-labeled probe, and 0.4 U Taq DNA polymerase per 10 μl. Each cycle is 30 sec long and consisted of denaturation at 94° C. followed by a 20 sec combined annealing/extension step at 60° C. The temperature transition rate between steps is 20° C./sec. After 60 cycles, a melting curve is acquired as follows: heating from 50-65° C. at 0.5° C./sec, 65-75° C. at 0.1° C./sec, and 75-94° C. at 0.5° C./sec. After baseline subtraction and conversion to melting peaks, all possible genotypes are more easily distinguished using the primers and/or probes of the preferred embodiment, compared to the published method. The next example describes the use of the oligonucleotides described herein in conjunction with a single melting curve assay to identify a SNP associated with Hereditary hemochromatosis.

EXAMPLE 10

Minor Groove binders are dsDNA-binding dyes. They are thought to bind to the minor groove of dsDNA and upon binding increase their fluorescence over a hundred fold. An example of such a dye is SYBR Green I™. These dyes are compatible with PCR up to a point, but at very high concentrations may start to inhibit the PCR reaction. SYBR can be used with the LightCycler™ in channel F1. An important quality of these dyes is that they bind to any dsDNA. The specific product, non-specific products, and primer dimers are detected equally well. Therefore, it is important that the PCR reaction is extremely "clean" and does not contain any dimers or non-specific products. The primers of the preferred embodiment can be used in any PCR reaction with a minor groove binder to make the method more specific. The embodied method is as described in Kutyavin, et al. U.S. Pat. No. 6,084,102, issued Jul. 4, 2000 (herein expressly incorporated by reference) except that the oligonucleotides described herein are used.

In particular, a single melting curve assay such as that in the reference, Donohue et al. *Clin Chem* 2000; 46:1540-7 is used for the rapid detection of the HFE C282Y mutation that utilizes real-time multiplex, allele-specific PCR and melting curves but requires neither fluorescent hybridization probes nor any postamplification manual processing. In particular, this C282Y genotyping assay requires the design of two unlabeled allele-specific sense-strand PCR primers (and a common antisense primer) to specifically amplify (in the same tube) either the C282 or Y282 allele (or both, in the case of heterozygotes).

Nonspecific amplification of the "other" allele is prevented by several deliberate nucleotide mismatches in both allele-specific primers. During and after PCR amplification in a thermal cycler with real-time fluorescent monitoring capabilities, the amplicons are detected fluorescently, not by expensive fluorescently labeled probes, but by a nonspecific double-stranded DNA binding dye (SYBR Green I) included in the reaction. Because one of the allele-specific primers is engineered with a long 5' GC tail to increase the melting temperature of its PCR product, the mutant- and wild-type-specific amplicons are discriminated by a progressive post-PCR temperature surge (with continuous fluorescence monitoring) to generate melting curves with characteristic allele-specific melting temperatures. The example below describes in greater detail the preparation of chips or arrays containing the oligonucleotides described herein.

EXAMPLE 11

The oligonucleotide probes described herein are particularly adaptable to current state-of-the-art chip based hybridization technologies. For example, for detection of the HMF mutation, a chip is prepared containing nucleic acids isolated from the blood samples taken from a large number of patients. Probes that are manufactured in accordance with the teachings herein are then used to detect either the C282 or Y282 allele or both. Accordingly, those individuals that have the HMF mutation are identified by virtue of the hybridization of the probe to the target sequence. In the same way, individuals who are wildtype may be identified by the presence of the wildtype allele or by the absence of a mutant allele.

Alternatively, an array can be prepared with the oligonucleotides of the present invention. A typical conventional array may contain 8-16 different oligonucleotides from each gene, for example. By using the oligonucleotides of the present invention, however, chips can be made using only 4 different oligonucleotides from each gene, thereby reducing the cost of analysis.

EXAMPLE 12

An example showing that when using Table 1, 2-Thio-dT offers better discrimination between A and G than the natural base T.

The sequences are derivatives of from Guo et al. U.S. Pat. No. 5,780,233. Oasis 3354 is identical to Guo SEQ. ID NO: 4 (identified herein as SEQ ID NO: 38). Oasis 3353 is a single 2-thio-dT substitution (upper case T) into Guo SEQ. ID NO: 4 (identified herein as SEQ ID NO: 39). Oasis 3355 is identical to Guo SEQ. ID NO: 5, but written below in the 5'-3' orientation (identified herein as SEQ ID NO: 40). Oasis 3356 contains a single mutation of G substituted for A (bold letters) (identified herein as SEQ ID NO: 41). All molecules are DNA:

```
3353  5'tggTtatagaagtat      15 mer 2-thio-T probe (SEQ ID NO: 46)

3354  5'tggttatagaagtat      15 mer unmod. Probe   (SEQ ID NO: 47)

3355  5'agatacttctataaccaagag  wt target          (SEQ ID NO: 48)

3356  5'agatacttctatagccaagag  mut target         (SEQ ID NO: 49)
```

These molecules were used in optical melting experiments in the following buffer: 1×SSCKM (150 NaCl, 25 mM NaCitrate, 80 mM KCl and 10 mM MgCl2, pH=7.4 at 20° C.).

Melting temperature determination (Tm° C.) results:

| | |
|---|---|
| 3353/3355 (2-thio-T probe/wt A target) | Tm = 46.8 |
| 3354/3355 (unmod T probe/wt A target) | Tm = 46.7 |

Accordingly, under these buffer conditions 2-thio-dT does not bind dA more or less tightly than dT as shown by the equivalent melting temperatures.

Melting temperature determination (Tm° C.) results:

| | |
|---|---|
| 3353/3356 (2-thio-T probe/mut G target) | Tm = 40.7 |
| 3354/3356 (unmod T probe/mut G target) | Tm = 42.6 |

Thus, under these buffer conditions a 2-thio-dT mismatch to dG is more discriminatory than a natural dT:dG mismatch, resulting in a melting temperature 2° C. lower. For this reason, a 2-thio-dT-containing probe has greater sequence specificity and greater allele specificity.

The utility of this observation in probe design is born out by the following comparison of the same data:

Melting temperature determination (Tm° C.) results:

| | |
|---|---|
| 3353/3355 (2-thio-T probe/wt A target) | Tm = 46.8 |
| 3353/3356 (2-thio-T probe/mut G target) | Tm = 40.7 |
| | ΔTm = 6° C. |
| 3354/3355 (unmod T probe/wt A target) | Tm = 46.7 |
| 3354/3356 (unmod T probe/mut G target) | Tm = 42.6 |
| | ΔTm = 4° C. |

One can readily see that a probe containing a 2-thio-dT substitution in the SNP position yields greater discrimination between two targets containing A versus G (ΔTm=6° C.) than natural dT (ΔTm=4° C.). An example of choosing an unnatural base from Table 1 for a G to A SNP is shown in Example 13.

EXAMPLE 13

The human hemochromatosis gene (HFE, accession no. XM_004413.3) is a clinically important gene and several research groups have published diagnostic assay procedures hoping to establish routine clinical screening for the presence of mutated HFE genes in the general population. Mutations in HFE cause iron accumulation that can lead to serious illness and even death.

One of the most frequent mutations is a G to A base change (G845A at position 1066). If the wild type and mutant alleles need to be detected, or diagnosed, on the basis of the SNP at position 1066 (shown below), the SNP Discrimination Table can be used to design more discriminatory probes than those based on natural bases alone (where C=5-methyl-dC and T=2-thio-dT).

Wild type allele (5'-3'):
1041 cctggggaag agcagagata tacgtgccag gtggagcacc caggcctgga (SEQ ID NO: 50)

Mutant allele (5'-3'):
1041 cctggggaag agcagagata tacgtaccag gtggagcacc caggcctgga (SEQ ID NO: 51)

Probe Design to Detect the Wild Type Allele.

The natural base to bind is G and the natural base to not bind is A, thus we have the following evolution of probe sequence selections:

| | |
|---|---|
| 5' c ctggcacgta tatctctgct ct conventional, low disc. | (SEQ ID NO: 52) |
| 5' c ctggcacgtB BBBBtctgct ct Universal base | (SEQ ID NO: 53) |
| 5' c ctggCacgtB BBBBtctgct ct UB with SNP disc. | (SEQ ID NO: 54) |

Probe Design to Detect the Mutant Allele

The natural base to bind is A and the natural base to not bind is G, thus we have the following evolution of probes:

| | |
|---|---|
| 5' c ctggtacgta tatctctgct ct conventional, low disc. | (SEQ ID NO: 55) |
| 5' c ctggtacgtB BBBBtctgct ct Universal base | (SEQ ID NO: 56) |
| 5' c ctggTacgtB BBBBtctgct ct UB with SNP disc. | (SEQ ID NO: 57) |

The use of the 5-methyl-dC and 2-thio-dT come directly from looking at the table axes as they are labeled, which natural bases to bind versus which natural bases to avoid. The combination of the non-hydrogen bonding universal bases with the unnatural bases in the SNP position should produce probes far superior to the conventional, low discrimination probes.

The following example demonstrates the use of oligonucleotides having juxtaposed universal bases to increase specificity for a target sequence.

EXAMPLE 14

Two sets of probes were used to detect polymorphisms in target DNA sequences. A first "improved" set of probes included oligonucleotides containing universal bases. A second "natural" set of probes contained only naturally occurring bases. Each set of immobilized probe pairs was used to detect single nucleotide polymorphisms (SNPs) in fluorescently labeled target oligonucleotides.

Natural probe pairs and Improved probe pairs consist of one probe oligonucleotide which formed perfect base-pairing, and one probe which contained one mismatched base-pairing when hybridized to the target oligonucleotide. The Improved probe pairs contained a variable number of artificial base mismatches using base analogues other than G, A, T, U or C such as generic, universal or degenerate bases.

The Improved probes and natural probes used in the microarray analysis were 5'-amine modified oligonucleotides. They were prepared to a final concentration of 30 uM in array printing buffer (150 mM sodium phosphate, pH8.5), and printed on to 3D-Link activated slides (Motorola Life Sciences, product # DN01-0025) by using a manual glass slide microarrayer system with a floating pin replicator (VP-scientific, product # VP478) and a glass slide indexer (VP-scientific, product # VP470) used according to the arrayer instructions.

After printing, slides were coupled and blocked according to the glass slide manufacture's recommended procedure (Motorola Life Sciences, product # DN01005). Briefly, freshly printed slides were incubated in a saturated NaCl chamber overnight to allow the 5'-amine-oligonucleotides to conjugate to the slide surface. Excess reactive surface sights were blocked after conjugation with pre-warmed blocking solution (0.1 M Tris, 50 mM ethanolamine, 0.1% SDS, pH 9.0) at 50° C. for 15 minutes, followed by a 4×SSC/0.1% SDS wash for 60 minutes.

The targets used in the microarray assays were 5'-fluorescent labeled oligonucleotides that contained single nucleotide polymorphism (SNP) sites. They were prepared to a final concentration of 10 uM in hybridization solution (5×SSC, 0.1 mg/ml salmon sperm DNA, 0.1% SDS or 0.05% Triton X-100). A cover slide (LifterSlip by Erie Scientific Co., product #22IX25-2-4635) was used to cover the array area on the slide and hold ~20 ul of hybridization solution.

The whole slide set was then kept in a hybridization cassette (TeleChem, product # AHC) for 2 hrs at various temperature (ranging from room temperature to 50° C.) followed by a 10-minute wash with washing solution (2×, 4× or 5×SSC, 0.1% SDS or 0.05% TritonX-100) at the hybridization temperature. The fluorescent signal on the slide was monitored by a fluorescent microscope (Nikon, Labophot-2), and the image was taken by digital camera (CoolSnap HQ) and analyzed by the MetaMorph image analysis program (Universal Imaging Corporation).

Immobilized Improved probes and natural probes were evaluated for hybridization between three SNP target fragment oligonucleotides from the human hemochromatosis gene (SNPs A, B and C). The hybridization specificity is presented as the ratio of perfect match (abbreviated as 'pm') to mismatch (abbreviated as 'mm') hybridization.

The oligonucleotide sequences of the target mimics and probes used are listed below. The SNP site of each oligo is underlined.

The following are target oligonucleotides with a phosphodiester backbone and FAM (abbreviated as 'F') label at the 5' terminus.

3533: 5' F-CAGGCCTGGGTGCTCCACCTGG<u>C</u>ACGTATATCTCTGCTC 3'  (SEQ ID NO: 58)

3534: 5' F-CAGGCCTGGGTGCTCCACCTGG<u>T</u>ACGTATATCTCTGCTC 3'  (SEQ ID NO: 59)

3535: 5' F-GTTCGGGGCTCCACACGGCGAC<u>T</u>CTCATGATCATAGAAC 3'  (SEQ ID NO: 60)

3536: 5' F-GTTCGGGGCTCCACACGGCGAC<u>A</u>CTCATGATCATAGAAC 3'  (SEQ ID NO: 61)

3537: 5' F-GGCTCCACACGGCGACTCTCAT<u>G</u>ATCATAGAACACGAACA 3'  (SEQ ID NO: 62)

3538: 5' F-GGCTCCACACGGCGACTCTCAT<u>C</u>ATCATAGAACACGAACA 3'  (SEQ ID NO: 63)

The following are natural oligonucleotide probes with a phosphodiester backbone and C6-amino linker (abbreviated as 'NH2-C6') followed by a spacer of four hexaethylene glycol molecules (PEG-282, abbreviated as 'S18') at the 5' terminus.

3569: 5' NH2-C6-S18-S18-S18-S18-TATACGT<u>G</u>CCGGTGG 3'  (SEQ ID NO: 64)

3570: 5' NH2-C6-S18-S18-S18-S18-TATACGT<u>A</u>CCGGTGG 3'  (SEQ ID NO: 65))

3571: 5' NH2-C6-S18-S18-S18-S18-GATCATGAG<u>A</u>GTCGCCGTG 3'  (SEQ ID NO: 66)

3572: 5' NH2-C6-S18-S18-S18-S18-GATCATGAG<u>T</u>GTCGCCGTG 3'  (SEQ ID NO: 67)

3573: 5' NH2-C6-S18-S18-S18-S18-TTCTATGAT<u>C</u>ATGAGAGTC 3'  (SEQ ID NO: 68)

3574: 5' NH2-C6-S18-S18-S18-S18-TTCTATGAT<u>G</u>ATGAGAGTC 3'  (SEQ ID NO: 69)

The following are improved probes with a phosphodiester backbone and C6-amino linker (abbreviated as 'NH2-C6') followed by either a spacer of four hexaethylene glycol (PEG-282, abbreviated as 'S18') residues or twelve deoxythymidine (abbreviated as 'T12') residues at the 5' terminus. The nucleotides with universal bases used in probes are 5'-nitroindole-2'-deoxyriboside (abbreviated as 'B'), 3-nitropyrrole-2'-deoxyriboside (abbreviated as 'M'), 7-deaza-2'-deoxyadenosine (abbreviated as 'A$^7$'), 2-amino-2'-deoxyadenosine (abbreviated as 'A$^2$'), 2-thiothymidine (abbreviated as 'T$^2$').

3419: 5' NH2-C6-T12-TACGT<u>G</u>CCBBBBBGAGCACCC 3'  (SEQ ID NO: 70)

3420: 5' NH2-C6-T12-TACGT<u>A$^7$</u>CCBBBBBGAGCACCC 3'  (SEQ ID NO: 71)

3421: 5' NH2-C6-T12-TACGT<u>G</u>CCBBBBBGAGCACC 3'  (SEQ ID NO: 72)

3422: 5' NH2-C6-T12-TACGT<u>A$^7$</u>CCBBBBBGAGCACC 3'  (SEQ ID NO: 73)

3575: 5' NH2-C6-S18-S18-S18-S18-TACGT<u>G</u>CCBBBBBGAGCACC 3'  (SEQ ID NO: 74)

3576: 5' NH2-C6-S18-S18-S18-S18-TACGT<u>A</u>CCBBBBBGAGCACC 3'  (SEQ ID NO: 75)

3581: 5' NH2-C6-S18-S18-S18-S18-TACGT<u>G</u>CCBBBMBGAGCACC 3'  (SEQ ID NO: 76)

3582: 5' NH2-C6-S18-S18-S18-S18-TACGT<u>A</u>CCBBBMBGAGCACC 3'  (SEQ ID NO: 77)

3423: 5' NH2-C6-T12-ATGAG<u>A$^2$</u>GTBBBBBTGTGGAGC 3'  (SEQ ID NO: 78)

3424: 5' NH2-C6-T12-ATGAG<u>T$^2$</u>GTBBBBBTGTGGAGC 3'  (SEQ ID NO: 79)

3425: 5' NH2-C6-T12-CTATGABBBBBAG<u>A$^2$</u>GTBBBBBTGTGGA 3'  (SEQ ID NO: 80)

3426: 5' NH2-C6-T12-CTATGABBBBBAG<u>T$^2$</u>GTBBBBBTGTGGA 3'  (SEQ ID NO: 81)

3589: 5' NH2-C6-S18-S18-S18-S18-TTCTATGABBBBBAG<u>A$^2$</u>GTBBBBBTGTGGAGC 3'  (SEQ ID NO: 82)

3590: 5' NH2-C6-S18-S18-S18-S18-TTCTATGABBBBBAG<u>T$^2$</u>GTBBBBBTGTGGAGC 3'  (SEQ ID NO: 83)

3591: 5' NH2-C6-S18-S18-S18-S18-TCGTGTTBBBBBAT<u>C</u>ATGAG 3'  (SEQ ID NO: 84)

3592: 5' NH2-C6-S18-S18-S18-S18-TCGTGTTBBBBBAT<u>G</u>ATGAG 3'  (SEQ ID NO: 85)

The following are improved probes with a hybrid backbone of phosphodiester and 2'-O-Methyl-RNA (abbreviated as 'N°').

```
#3539: 5' NH2-C6-S18-S18-S18-S18-U°A°C°G°U°GCCBBBBBGAGCACC 3'    (SEQ ID NO: 86)

#3540: 5' NH2-C6-S18-S18-S18-S18-U°A°C°G°U°ACCBBBBBGAGCACC 3'    (SEQ ID NO: 87)

#3521: 5' NH2-C6-S18-S18-S18-S18-TACGTGCCBBBBBG°A°G°C°A°C°C°C° 3'    (SEQ ID NO: 88)

#3522: 5' NH2-C6-S18-S18-S18-S18-TACGTACCBBBBBG°A°G°C°A°C°C°C° 3'    (SEQ ID NO: 89)

#3541: 5' NH2-C6-S18-S18-S18-S18-A°U°G°A°G°A²GTBBBBBTGTGGAGCA 3'    (SEQ ID NO: 90)

#3542: 5' NH2-C6-S18-S18-S18-S18-A°U°G°A°G°T²GTBBBBBTGTGGAGC 3'    (SEQ ID NO: 91)

#3529: 5' NH2-C6-S18-S18-S18-S18-ATGATCATBBBBBBC°G°C°C°G°U°G°U° 3'    (SEQ ID NO: 92)

#3530: 5' NH2-C6-S18-S18-S18-S18-ATGATGATBBBBBBC°G°C°C°G°U°G°U° 3'    (SEQ ID NO: 93)
```

The results of the hybridization specificity of natural probes and Improved probes are listed in Table 5.

TABLE 5

| Probe Type | # pm | # mm | Specificity Ratio | Condition Temperature | Salt in washing |
|---|---|---|---|---|---|
| site A, wild type target (#3533) | | | | | |
| natural | 3569 | 3570 | 5 | 50° C. | 2X SSC |
| Improved probe | 3539 | 3540 | 10 | R° T | 5X SSC |
| site A, mutant target (#3534) | | | | | |
| natural | 3570 | 3569 | 1.5 | 50° C. | 2X SSC |
| Improved probe | 3540 | 3539 | 30 | 45° C. | 2X SSC |
| Improved probe | 3522 | 3521 | 30 | 45° C. | 2X SSC |
| Improved probe | 3420 | 3419 | 15 | 45° C. | 2X SSC |
| Improved probe | 3422 | 3421 | 18 | 45° C. | 2X SSC |
| Improved probe | 3582 | 3581 | 23 | 37° C. | 5X SSC |
| Improved probe | 3576 | 3575 | 15 | 30° C. | 5X SSC |
| site B, wild type target (#3535) | | | | | |
| natural | 3571 | 3572 | 1 | 50° C. | 2-5X SSC |
| Improved probe | 3541 | 3542 | 22 | 45° C. | 2X SSC |
| Improved probe | 3541 | 3542 | 15 | 30° C. | 2X SSC |
| Improved probe | 3523 | 3524 | 6 | 30° C. | 2X SSC |
| Improved probe | 3525 | 3526 | 14 | 37° C. | 4X SSC |
| Improved probe | 3589 | 3590 | 3 | 37° C. | 5X SSC |
| site B, mutant target (#3536) | | | | | |
| natural | 3572 | 3571 | 1 | 50° C. | 2-5X SSC |
| Improved probe | 3542 | 3541 | 54 | 45° C. | 4X SSC |
| Improved probe | 3524 | 3523 | 3 | 45° C. | 4X SSC |
| Improved probe | 3426 | 3425 | 8 | 45° C. | 2X SSC |
| Improved probe | 3426 | 3425 | 5 | 30° C. | 5X SSC |
| Improved probe | 3590 | 3589 | 5 | 37° C. | 5X SSC |
| site C, wild type target (#3537) | | | | | |
| natural | 3573 | 3574 | 9 | 50° C. | 2X SSC |
| Improved probe | 3591 | 3592 | 7 | R° T | 5X SSC |
| Improved probe | 3529 | 3530 | 12 | 37° C. | 5X SSC |
| site C, mutant target (#3538) | | | | | |
| natural | 3574 | 3573 | 11 | 50° C. | 2X SSC |
| Improved probe | 3592 | 3591 | 30 | 45° C. | 2X SSC |
| Improved probe | 3592 | 3591 | 45 | R° T | 5X SSC |

The results indicated that Improved probe sets having juxtaposed universal bases had improved hybridization specificity when compared to natural probe sets in all cases. The natural probe sets used were designed with a SNP site in the middle and optimized to give the best differential hybridization between pm and mm, but were not all capable of showing good discrimination. Improved probe sets with a block of universal bases at the 5' and/or 3' to the SNP site, with two or more universal base blocks, and other unnatural bases, significantly increased hybridization specificity to discriminate mm from pm, even in the case where the natural probe sets showed good discrimination.

Within this application, unless otherwise stated, the techniques utilized may be found in any of several well-known references including: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), Berger et al., Guide to Molecular Cloning Techniques, Methods in Enzymology, Vol. 152, Academic Press, Inc., (1987); Davis et al., Basic Methods in Molecular Biology, Elsevier Science Publishing Co., Inc. (1986); Ausubel et al., Short Protocols in Molecular Biology, 2nd ed., John Wiley & Sons, (1992), Grinsted et al., Plasmid Technology, Methods in Microbiology, Vol. 21, Academic Press, Inc., (1988); Symonds et al., Phage Mu, Cold Spring Harbor Laboratory Press (1987), Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2.sup.nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The basic principles of eukaryotic gene structure and expression are generally known in the art. (See for example Hawkins, Gene Structure and Expression, Cambridge University Press, Cambridge, UK, 1985; Alberts et al., The Molecular Biology of the Cell, Garland Press, New York, 1983; Goeddel, Gene Expression Technology, Methods in Enzymology, Vol. 185, Academic Press, Inc., (1991); Lewin, Genes VI, Oxford Press, Oxford, UK, 1998). Each of the above-mentioned references are hereby incorporated by reference in their entirety.

Although the invention has been described with reference to embodiments and examples, it should be understood that various modifications can be made without departing from the spirit of the invention. All references cited herein are hereby expressly incorporated by reference.

What is claimed is:

1. An oligonucleotide probe for detecting a first target nucleic acid sequence comprising the formula:

XRY wherein X comprises between about 5 and 20 modified nucleic acid bases complementary to a first region of said first target nucleic acid sequence;
wherein R comprises between about 5 and 10 universal or generic bases juxtaposed to one another and said universal or generic bases align with bases of a second region of said first target nucleic acid sequence;
wherein Y comprises between about 5 and about 20 nucleic acid bases complementary to a third region of said first target nucleic acid sequence;
wherein X, R, and Y are covalently joined;
wherein greater than 20% of the total number of bases in said oligonucleotide probe are said universal or generic bases juxtaposed to one another;
wherein said oligonucleotide probe further comprises a detectable label; and
wherein said oligonucleotide probe is capable of hybridizing to and detecting said first target nucleic acid sequence but not able to detect a second target nucleic acid sequence that differs from said first target nucleic acid sequence by a single nucleotide base mismatch in the first or third region of the target nucleic acid sequence.

2. An oligonucleotide probe for distinguishing a first target nucleic acid sequence from a second target nucleic acid sequence that differs from said first target nucleic acid sequence by a nucleotide base mismatch, said oligonucleotide probe comprising a site complementary to said first target nucleic acid sequence, said site having a 5' and 3' side thereto and having a non-complementary base to said mismatch of said second target nucleic acid sequence;

at least five universal or generic bases juxtaposed to one another, said universal or generic bases being located on the 5' or 3' side of said site and aligned with bases of the first target nucleic acid sequence;

a first region complementary to a first region of the first target nucleic acid and a second region complementary to a second region of the first target nucleic acid, said first and second regions being located on the 5' and 3' side of said site, respectively;

wherein said oligonucleotide probe has between about 10 and 25 bases;

wherein said oligonucleotide probe further comprises a detectable label;

and wherein said probe detects said first target nucleic acid sequence and does not detect said second target sequence.

3. The oligonucleotide probe of claim 1, wherein at least 6 of said bases are universal or generic bases juxtaposed to one another.

4. The oligonucleotide probe of claim 1, wherein at least 7 of said bases are universal or generic bases juxtaposed to one another.

5. The oligonucleotide probe of claim 1 wherein said universal bases are selected from the group consisting of: 2-deoxyinosine, 5-nitroindole, 3-nitropyrrole, and 2-deoxynebularine.

6. The oligonucleotide probe of claim 1, wherein said oligonucleotide probe comprises between about 10 and about 25 bases.

7. The oligonucleotide probe of claim 1, wherein said oligonucleotide probe comprises between about 10 and about 50 bases.

8. The oligonucleotide probe of claim 1, further comprising a non-nucleic acid linker.

9. The oligonucleotide probe of claim 1, wherein 30% or more of said bases are universal or generic bases.

10. A hybrid consisting of the oligonucleotide probe of claim 1 and a target nucleic acid sequence.

11. The oligonucleotide probe of claim 1, wherein said oligonucleotide probe has an increased ability to distinguish said first target nucleic acid sequence from said second target nucleic acid sequence that differs from said first target nucleic acid sequence by a nucleotide base mismatch as compared to an oligonucleotide probe that does not have any universal or generic bases.

12. The oligonucleotide probe of claim 2, wherein at least 6 of said bases are universal or generic bases juxtaposed to one another.

13. The oligonucleotide probe of claim 2, wherein at least 7 of said bases are universal or generic bases juxtaposed to one another.

14. The oligonucleotide probe of claim 2 wherein said universal bases are selected from the group consisting of: 2-deoxyinosine, 5-nitroindole, 3-nitropyrrole, and 2-deoxynebularine.

15. The oligonucleotide probe of claim 2, wherein said oligonucleotide probe comprises between about 10 and about 50 bases.

16. The oligonucleotide probe of claim 2, further comprising a non-nucleic acid linker.

17. The oligonucleotide probe of claim 2, wherein greater than 20% of said bases are universal or generic bases.

18. The oligonucleotide probe of claim 2, wherein 30% or more of said bases are universal or generic bases.

19. A hybrid consisting of the oligonucleotide probe of claim 2 and a target nucleic acid sequence.

20. The oligonucleotide probe of claim 2, wherein said oligonucleotide probe has an increased ability to distinguish said first target nucleic acid sequence from said second target nucleic acid sequence that differs from said first target nucleic acid sequence by a nucleotide base mismatch as compared to an oligonucleotide probe that does not have any universal or generic bases.

21. The oligonucleotide probe of claim 1 or 2, wherein said universal bases are selected from the group consisting of: 2-deoxyinosine and 2-deoxynebularine.

22. The oligonucleotide probe of claim 1 or 2, wherein said universal bases are 3-nitropyrrole.

23. The oligonucleotide probe of claim 1 or 2, wherein said universal bases are 5-nitroindole.

* * * * *

SEQUENCE LISTING

<160> NUMBER OF SEQ ID NOS: 94

<210> SEQ ID NO 1
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 21
<223> OTHER INFORMATION: n = modified base

<400> SEQUENCE: 1
ctgctaactg agcacaggat n                                              21

<210> SEQ ID NO 2
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 21
<223> OTHER INFORMATION: n = modified base

<400> SEQUENCE: 2
gagctgctaa ctgagcacag n                                              21

<210> SEQ ID NO 3
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 7, 17
<223> OTHER INFORMATION: n = modified base

<400> SEQUENCE: 3
ctgctangca caggatn                                                   17

<210> SEQ ID NO 4
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 11, 17
<223> OTHER INFORMATION: n = modified base

<400> SEQUENCE: 4
gagctgctaa ncacagn                                                   17

<210> SEQ ID NO 5
<211> LENGTH: 15
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 8, 15
<223> OTHER INFORMATION: n = modified base

```
<400> SEQUENCE: 5
gctgctangc acagn                                                       15

<210> SEQ ID NO 6
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 9, 17
<223> OTHER INFORMATION: n = modified base

<400> SEQUENCE: 6
gagctgctna gcacagn                                                     17

<210> SEQ ID NO 7
<211> LENGTH: 37
<212> TYPE: DNA
<213> ORGANISM: Artificial Sequence
<220> FEATURE:
<223> OTHER INFORMATION: Artificial Oligonucleotide

<400> SEQUENCE: 7
tactcgacga ttgactcgtg tcctactgga ccctggg                               37

<210> SEQ ID NO 8
<211> LENGTH: 37
<212> TYPE: DNA
<213> ORGANISM: Artificial Sequence
<220> FEATURE:
<223> OTHER INFORMATION: Artificial Oligonucleotide

<400> SEQUENCE: 8
tactcgagga ttgactcgtg tcctactgga ccctggg                               37

<210> SEQ ID NO 9
<211> LENGTH: 23
<212> TYPE: DNA
<213> ORGANISM: Artificial Sequence
<220> FEATURE:
<223> OTHER INFORMATION: Artificial Oligonucleotide

<400> SEQUENCE: 9
tacgtgccag gtggagcacc cag                                              23

<210> SEQ ID NO 10
<211> LENGTH: 23
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 12
<223> OTHER INFORMATION: n = modified base

<400> SEQUENCE: 10
tacgtgccag gnggagcacc cag                                              23

<210> SEQ ID NO 11
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
```

```
<221> NAME/KEY: misc_feature
<222> LOCATION: 11
<223> OTHER INFORMATION: n = modified base

<400> SEQUENCE: 11
tacgtgccag ngagcaccca g                                              21

<210> SEQ ID NO 12
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 10
<223> OTHER INFORMATION: n = modified base

<400> SEQUENCE: 12
tacgtgccan agcacccag                                                 19

<210> SEQ ID NO 13
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 9
<223> OTHER INFORMATION: n = modified base

<400> SEQUENCE: 13
tacgtgccng cacccag                                                   17

<210> SEQ ID NO 14
<211> LENGTH: 15
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 8
<223> OTHER INFORMATION: n = modified base

<400> SEQUENCE: 14
tacgtgcnca cccag                                                     15

<210> SEQ ID NO 15
<211> LENGTH: 13
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 7
<223> OTHER INFORMATION: n = modified base

<400> SEQUENCE: 15
tacgtgnacc cag                                                       13

<210> SEQ ID NO 16
<211> LENGTH: 29
<212> TYPE: DNA
<213> ORGANISM: Artificial Sequence
<220> FEATURE:
<223> OTHER INFORMATION: Artificial Oligonucleotide
```

```
<400> SEQUENCE: 16
gcctgggtgc tccacctggc acgtatatc                                    29

<210> SEQ ID NO 17
<211> LENGTH: 29
<212> TYPE: DNA
<213> ORGANISM: Artificial Sequence
<220> FEATURE:
<223> OTHER INFORMATION: Artificial Oligonucleotide

<400> SEQUENCE: 17
gcctgggtgc tccacctggt acgtatatc                                    29

<210> SEQ ID NO 18
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 18
ctcttgagag agctagtatc t                                            21

<210> SEQ ID NO 19
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 7, 15
<223> OTHER INFORMATION: n = modified base

<400> SEQUENCE: 19
ctcttgngag agctngtatc t                                            21

<210> SEQ ID NO 20
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 6, 16
<223> OTHER INFORMATION: n = modified base

<400> SEQUENCE: 20
ctcttnagag agctantatc t                                            21

<210> SEQ ID NO 21
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 5, 17
<223> OTHER INFORMATION: n = modified base

<400> SEQUENCE: 21
ctctngagag agctagnatc t                                            21

<210> SEQ ID NO 22
<211> LENGTH: 18
<212> TYPE: DNA
```

```
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 5, 15
<223> OTHER INFORMATION: n = modified base

<400> SEQUENCE: 22
ctctnagaga gctantct                                                    18

<210> SEQ ID NO 23
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 5, 14
<223> OTHER INFORMATION: n = modified base

<400> SEQUENCE: 23
ctctngagag ctanatct                                                    18

<210> SEQ ID NO 24
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 14
<223> OTHER INFORMATION: n = modified base

<400> SEQUENCE: 24
ctcttgagag agcntct                                                     17

<210> SEQ ID NO 25
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4
<223> OTHER INFORMATION: n = modified base

<400> SEQUENCE: 25
ctcnagagct agtatct                                                     17

<210> SEQ ID NO 26
<211> LENGTH: 16
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4, 10
<223> OTHER INFORMATION: n = modified base

<400> SEQUENCE: 26
ctcnagagcn gtatct                                                      16

<210> SEQ ID NO 27
<211> LENGTH: 16
<212> TYPE: DNA
```

```
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4, 11
<223> OTHER INFORMATION: n = modified base

<400> SEQUENCE: 27
ctcngagagc ntatct                                                    16

<210> SEQ ID NO 28
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 28
agatactagc gctctcaaga g                                              21

<210> SEQ ID NO 29
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 29
agatactagc tcgctcaaga g                                              21

<210> SEQ ID NO 30
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 30
agatactagc tctctcaaga g                                              21

<210> SEQ ID NO 31
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 31
ctcttgagag agctagtatc t                                              21

<210> SEQ ID NO 32
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 7, 15
<223> OTHER INFORMATION: n = modified base

<400> SEQUENCE: 32
ctcttgngag agctngtatc t                                              21

<210> SEQ ID NO 33
<211> LENGTH: 21
<212> TYPE: DNA
```

<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 6, 16
<223> OTHER INFORMATION: n = modified base

<400> SEQUENCE: 33
ctcttnagag agctantatc t                                              21

<210> SEQ ID NO 34
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 5, 17
<223> OTHER INFORMATION: n = modified base

<400> SEQUENCE: 34
ctctngagag agctagnatc t                                              21

<210> SEQ ID NO 35
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 5, 15
<223> OTHER INFORMATION: n = modified base

<400> SEQUENCE: 35
ctctnagaga gctantct                                                  18

<210> SEQ ID NO 36
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 5, 14
<223> OTHER INFORMATION: n = modified base

<400> SEQUENCE: 36
ctctngagag ctanatct                                                  18

<210> SEQ ID NO 37
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 14
<223> OTHER INFORMATION: n = modified base

<400> SEQUENCE: 37
ctcttgagag agcntct                                                   17

<210> SEQ ID NO 38
<211> LENGTH: 17
<212> TYPE: DNA

```
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4
<223> OTHER INFORMATION: n = modified base

<400> SEQUENCE: 38
ctcnagagct agtatct                                                  17

<210> SEQ ID NO 39
<211> LENGTH: 16
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4, 10
<223> OTHER INFORMATION: n = modified base

<400> SEQUENCE: 39
ctcnagagcn gtatct                                                   16

<210> SEQ ID NO 40
<211> LENGTH: 16
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4, 11
<223> OTHER INFORMATION: n = modified base

<400> SEQUENCE: 40
ctcngagagc ntatct                                                   16

<210> SEQ ID NO 41
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 41
agatactagc gctctcaaga g                                             21

<210> SEQ ID NO 42
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 42
agatactagc tcgctcaaga g                                             21

<210> SEQ ID NO 43
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 43
agatactagc tctctcaaga g                                             21
```

```
<210> SEQ ID NO 44
<211> LENGTH: 23
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 17
<223> OTHER INFORMATION: n = modified base

<400> SEQUENCE: 44
tgaaggagaa ggtgtcngcg gga                                             23

<210> SEQ ID NO 45
<211> LENGTH: 25
<212> TYPE: DNA
<213> ORGANISM: Artificial Sequence
<220> FEATURE:
<223> OTHER INFORMATION: Artificial Oligonucleotide

<400> SEQUENCE: 45
cctcggctaa atagtagtgc gtcga                                           25

<210> SEQ ID NO 46
<211> LENGTH: 20
<212> TYPE: DNA
<213> ORGANISM: Artificial Sequence
<220> FEATURE:
<223> OTHER INFORMATION: Artificial Oligonucleotide

<400> SEQUENCE: 46
aggacggtgc ggtgagagtg                                                 20

<210> SEQ ID NO 47
<211> LENGTH: 14
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 4
<223> OTHER INFORMATION: n = modified base

<400> SEQUENCE: 47
tggnatagaa gtat                                                       14

<210> SEQ ID NO 48
<211> LENGTH: 15
<212> TYPE: DNA
<213> ORGANISM: Artificial Sequence
<220> FEATURE:
<223> OTHER INFORMATION: Artificial Oligonucleotide

<400> SEQUENCE: 48
tggttataga agtat                                                      15

<210> SEQ ID NO 49
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 49
agatacttct ataaccaaga g                                               21
```

```
<210> SEQ ID NO 50
<211> LENGTH: 21
<212> TYPE: DNA
<213> ORGANISM: Artificial Sequence
<220> FEATURE:
<223> OTHER INFORMATION: Artificial Oligonucleotide

<400> SEQUENCE: 50
agatacttct atagccaaga g                                             21

<210> SEQ ID NO 51
<211> LENGTH: 50
<212> TYPE: DNA
<213> ORGANISM: Artificial Sequence
<220> FEATURE:
<223> OTHER INFORMATION: Artificial Oligonucleotide

<400> SEQUENCE: 51
cctggggaag agcagagata tacgtgccag gtggagcacc caggcctgga              50

<210> SEQ ID NO 52
<211> LENGTH: 50
<212> TYPE: DNA
<213> ORGANISM: Artificial Sequence
<220> FEATURE:
<223> OTHER INFORMATION: Artificial Oligonucleotide

<400> SEQUENCE: 52
cctggggaag agcagagata tacgtaccag gtggagcacc caggcctgga              50

<210> SEQ ID NO 53
<211> LENGTH: 23
<212> TYPE: DNA
<213> ORGANISM: Artificial Sequence
<220> FEATURE:
<223> OTHER INFORMATION: Artificial Oligonucleotide

<400> SEQUENCE: 53
cctggcacgt atatctctgc tct                                           23

<210> SEQ ID NO 54
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 11
<223> OTHER INFORMATION: n = modified base

<400> SEQUENCE: 54
cctggcacgt ntctgctct                                                19

<210> SEQ ID NO 55
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 6, 11
<223> OTHER INFORMATION: n = modified base

<400> SEQUENCE: 55
cctggnacgt ntctgctc                                                 18
```

```
<210> SEQ ID NO 56
<211> LENGTH: 23
<212> TYPE: DNA
<213> ORGANISM: Artificial Sequence
<220> FEATURE:
<223> OTHER INFORMATION: Artificial Oligonucleotide

<400> SEQUENCE: 56
cctggtacgt atatctctgc tct                                           23

<210> SEQ ID NO 57
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 11
<223> OTHER INFORMATION: n = modified base

<400> SEQUENCE: 57
cctggtacgt ntctgctct                                                19

<210> SEQ ID NO 58
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 6, 11
<223> OTHER INFORMATION: n = modified base

<400> SEQUENCE: 58
cctggnacgt ntctgctct                                                19

<210> SEQ ID NO 59
<211> LENGTH: 39
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1
<223> OTHER INFORMATION: n = modified base

<400> SEQUENCE: 59
naggcctggg tgctccacct ggcacgtata tctctgctc                          39

<210> SEQ ID NO 60
<211> LENGTH: 39
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1
<223> OTHER INFORMATION: n = modified base

<400> SEQUENCE: 60
naggcctggg tgctccacct ggtacgtata tctctgctc                          39

<210> SEQ ID NO 61
<211> LENGTH: 39
<212> TYPE: DNA
```

<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1
<223> OTHER INFORMATION: n = modified base

<400> SEQUENCE: 61
nttcggggct ccacacggcg actctcatga tcatagaac        39

<210> SEQ ID NO 62
<211> LENGTH: 39
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1
<223> OTHER INFORMATION: n = modified base

<400> SEQUENCE: 62
nttcggggct ccacacggcg acactcatga tcatagaac        39

<210> SEQ ID NO 63
<211> LENGTH: 40
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1
<223> OTHER INFORMATION: n = modified base

<400> SEQUENCE: 63
ngctccacac ggcgactctc atgatcatag aacacgaaca        40

<210> SEQ ID NO 64
<211> LENGTH: 40
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1
<223> OTHER INFORMATION: n = modified base

<400> SEQUENCE: 64
ngctccacac ggcgactctc atcatcatag aacacgaaca        40

<210> SEQ ID NO 65
<211> LENGTH: 17
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2
<223> OTHER INFORMATION: n = modified base

<400> SEQUENCE: 65
nntatacgtg ccggtgg        17

<210> SEQ ID NO 66
<211> LENGTH: 17
<212> TYPE: DNA

<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2
<223> OTHER INFORMATION: n = modified base

<400> SEQUENCE: 66
nntatacgta ccggtgg                                                  17

<210> SEQ ID NO 67
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2
<223> OTHER INFORMATION: n = modified base

<400> SEQUENCE: 67
nngatcatga gagtcgccgt g                                             21

<210> SEQ ID NO 68
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2
<223> OTHER INFORMATION: n = modified base

<400> SEQUENCE: 68
nngatcatga gtgtcgccgt g                                             21

<210> SEQ ID NO 69
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2
<223> OTHER INFORMATION: n = modified base

<400> SEQUENCE: 69
nnttctatga tcatgagagt c                                             21

<210> SEQ ID NO 70
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2
<223> OTHER INFORMATION: n = modified base

<400> SEQUENCE: 70
nnttctatga tgatgagagt c                                             21

<210> SEQ ID NO 71
<211> LENGTH: 19
<212> TYPE: DNA

<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11
<223> OTHER INFORMATION: n = modified base

<400> SEQUENCE: 71
nntacgtgcc ngagcaccc                                                19

<210> SEQ ID NO 72
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 8, 11
<223> OTHER INFORMATION: n = modified base

<400> SEQUENCE: 72
nntacgtncc ngagcaccc                                                19

<210> SEQ ID NO 73
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11
<223> OTHER INFORMATION: n = modified base

<400> SEQUENCE: 73
nntacgtgcc ngagcacc                                                 18

<210> SEQ ID NO 74
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 8, 11
<223> OTHER INFORMATION: n = modified base

<400> SEQUENCE: 74
nntacgtncc ngagcacc                                                 18

<210> SEQ ID NO 75
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11
<223> OTHER INFORMATION: n = modified base

<400> SEQUENCE: 75
nntacgtgcc ngagcacc                                                 18

<210> SEQ ID NO 76
<211> LENGTH: 18
<212> TYPE: DNA

<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11
<223> OTHER INFORMATION: n = modified base

<400> SEQUENCE: 76
nntacgtacc ngagcacc                                                 18

<210> SEQ ID NO 77
<211> LENGTH: 20
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 12, 13
<223> OTHER INFORMATION: n = modified base

<400> SEQUENCE: 77
nntacgtgcc nnngagcacc                                               20

<210> SEQ ID NO 78
<211> LENGTH: 20
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 12, 13
<223> OTHER INFORMATION: n = modified base

<400> SEQUENCE: 78
nntacgtacc nnngagcacc                                               20

<210> SEQ ID NO 79
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 8, 11
<223> OTHER INFORMATION: n = modified base

<400> SEQUENCE: 79
nnatgagngt ntgtggagc                                                19

<210> SEQ ID NO 80
<211> LENGTH: 19
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 8, 11
<223> OTHER INFORMATION: n = modified base

<400> SEQUENCE: 80
nnatgagngt ntgtggagc                                                19

<210> SEQ ID NO 81
<211> LENGTH: 21
<212> TYPE: DNA

```
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 9, 12, 15
<223> OTHER INFORMATION: n = modified base

<400> SEQUENCE: 81
nnctatgana gngtntgtgg a                                              21

<210> SEQ ID NO 82
<211> LENGTH: 21
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 9, 12, 15
<223> OTHER INFORMATION: n = modified base

<400> SEQUENCE: 82
nnctatgana gngtntgtgg a                                              21

<210> SEQ ID NO 83
<211> LENGTH: 25
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 14, 17
<223> OTHER INFORMATION: n = modified base

<400> SEQUENCE: 83
nnttctatga nagngtntgt ggagc                                          25

<210> SEQ ID NO 84
<211> LENGTH: 25
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 14, 17
<223> OTHER INFORMATION: n = modified base

<400> SEQUENCE: 84
nnttctatga nagngtntgt ggagc                                          25

<210> SEQ ID NO 85
<211> LENGTH: 18
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 10
<223> OTHER INFORMATION: n = modified base

<400> SEQUENCE: 85
nntcgtgttn atcatgag                                                  18

<210> SEQ ID NO 86
<211> LENGTH: 18
<212> TYPE: DNA
```

```
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 10
<223> OTHER INFORMATION: n = modified base

<400> SEQUENCE: 86
nntcgtgttn atgatgag                                                  18

<210> SEQ ID NO 87
<211> LENGTH: 14
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 3, 7
<223> OTHER INFORMATION: n = modified base

<400> SEQUENCE: 87
nnngccngag cacc                                                      14

<210> SEQ ID NO 88
<211> LENGTH: 14
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 3, 7
<223> OTHER INFORMATION: n = modified base

<400> SEQUENCE: 88
nnnaccngag cacc                                                      14

<210> SEQ ID NO 89
<211> LENGTH: 12
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 12
<223> OTHER INFORMATION: n = modified base

<400> SEQUENCE: 89
nntacgtgcc nn                                                        12

<210> SEQ ID NO 90
<211> LENGTH: 12
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 12
<223> OTHER INFORMATION: n = modified base

<400> SEQUENCE: 90
nntacgtacc nn                                                        12

<210> SEQ ID NO 91
<211> LENGTH: 15
<212> TYPE: DNA
```

```
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 3, 4, 7
<223> OTHER INFORMATION: n = modified base

<400> SEQUENCE: 91
nnnngtntgt ggagc                                                    15

<210> SEQ ID NO 92
<211> LENGTH: 15
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 3, 4, 7
<223> OTHER INFORMATION: n = modified base

<400> SEQUENCE: 92
nnnngtntgt ggagc                                                    15

<210> SEQ ID NO 93
<211> LENGTH: 12
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 12
<223> OTHER INFORMATION: n = modified base

<400> SEQUENCE: 93
nnatgatcat nn                                                       12

<210> SEQ ID NO 94
<211> LENGTH: 12
<212> TYPE: DNA
<213> ORGANISM: Artificial Sequence
<220> FEATURE:
<223> OTHER INFORMATION: Artificial Oligonucleotide
<220> FEATURE:
<221> NAME/KEY: misc_feature
<222> LOCATION: 1, 2, 11, 12
<223> OTHER INFORMATION: n = modified base

<400> SEQUENCE: 94
nnatgatgat nn                                                       12
```